(12) United States Patent
Ye et al.

(10) Patent No.: US 11,839,145 B2
(45) Date of Patent: Dec. 5, 2023

(54) ORGANIC LIGHT EMITTING DIODE

(71) Applicant: Samsung Display Co., LTD., Yongin-si (KR)

(72) Inventors: Jimyoung Ye, Suwon-si (KR); Hyomin Ko, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 484 days.

(21) Appl. No.: 16/923,047

(22) Filed: Jul. 7, 2020

(65) Prior Publication Data

US 2021/0159418 A1 May 27, 2021

(30) Foreign Application Priority Data

Nov. 25, 2019 (KR) .......................... 10-2019-0152472

(51) Int. Cl.
H01L 51/50 (2006.01)
H10K 85/60 (2023.01)
(Continued)

(52) U.S. Cl.
CPC .......... *H10K 85/615* (2023.02); *C07C 211/06* (2013.01); *C07D 209/86* (2013.01); *C07D 401/12* (2013.01); *C07D 409/14* (2013.01); *C09K 11/06* (2013.01); *H10K 85/626* (2023.02); *H10K 85/633* (2023.02); *H10K 85/636* (2023.02); *H10K 85/6572* (2023.02); *C07C 2603/18* (2017.05); *C09K 2211/1007* (2013.01); *C09K 2211/1011* (2013.01);
(Continued)

(58) Field of Classification Search
CPC .......................... H10K 85/615; H10K 85/626
See application file for complete search history.

(56) References Cited

U.S. PATENT DOCUMENTS 8,530,888 B2 9/2013 Jeong et al.
9,093,650 B2 7/2015 Kim et al.
(Continued)

FOREIGN PATENT DOCUMENTS

JP 3856546 12/2006
KR 10-20110097044 8/2011
(Continued)

OTHER PUBLICATIONS

Kruzinauskiene et al., Synthetic Metals 157 (2007) 401-406.*
(Continued)

*Primary Examiner* — Anthony Ho
(74) *Attorney, Agent, or Firm* — H.C. Park & Associates, PLC

(57) ABSTRACT

An organic light emitting diode includes a first electrode, a hole transport region disposed on the first electrode, an emission layer disposed on the hole transport region, an electron transport region disposed on the emission layer, and a second electrode disposed on the electron transport region. The hole transport region includes a first hole transport layer which is directly disposed on the lower portion of the emission layer and has a first refractive index, and a second hole transport layer which is disposed on the lower portion of the first hole transport layer and has a second refractive index, thereby exhibiting an improved luminous efficiency characteristic.

17 Claims, 4 Drawing Sheets

(51) Int. Cl.
   *C09K 11/06* (2006.01)
   *C07D 209/86* (2006.01)
   *C07D 401/12* (2006.01)
   *C07D 409/14* (2006.01)
   *C07C 211/06* (2006.01)
   *H10K 50/155* (2023.01)
   *H10K 50/15* (2023.01)
   *H10K 102/00* (2023.01)

(52) U.S. Cl.
   CPC .... *C09K 2211/1018* (2013.01); *H10K 50/155* (2023.02); *H10K 50/156* (2023.02); *H10K 85/624* (2023.02); *H10K 85/654* (2023.02); *H10K 85/655* (2023.02); *H10K 2102/351* (2023.02)

(56) References Cited

U.S. PATENT DOCUMENTS

| | | | |
|---|---|---|---|
| 10,184,078 | B2 | 1/2019 | Matsuura et al. |
| 10,326,111 | B2 | 6/2019 | Yoo et al. |
| 10,756,275 | B2 | 8/2020 | Kato et al. |
| 2011/0198581 | A1 | 8/2011 | Yabunouchi et al. |
| 2011/0204342 | A1† | 8/2011 | Jeong |
| 2015/0008422 | A1 | 1/2015 | Lee et al. |
| 2015/0207084 | A1* | 7/2015 | Hwang ............... H01L 51/0085 257/40 |
| 2016/0043317 | A1† | 2/2016 | Takada |
| 2016/0133850 | A1† | 5/2016 | Matsuura |
| 2016/0197277 | A1† | 7/2016 | Kato |
| 2017/0018600 | A1 | 1/2017 | Ito et al. |
| 2017/0200899 | A1 | 7/2017 | Kim et al. |

FOREIGN PATENT DOCUMENTS

| | | |
|---|---|---|
| KR | 10-1317881 | 10/2013 |
| KR | 10-1325329 | 11/2013 |
| KR | 10-2016-0017596 | 2/2016 |
| KR | 10-2016-0055675 | 5/2016 |
| KR | 10-2017-0030450 | 3/2017 |
| KR | 10-1784804 | 10/2017 |
| KR | 20180082710 | † 7/2018 |
| KR | 10-1887237 | 8/2018 |
| TW | 201836186 | † 10/2018 |

OTHER PUBLICATIONS

Anonymous, Third Party Observation for application No. EP20210152336, 5 pages, Oct. 28, 2021, https://register.epo.org/application?documentId=KVAUF9NA5Z667NX&number=EP21152336&lng=en&npl=false.†

\* cited by examiner
† cited by third party

ORGANIC LIGHT EMITTING DIODE

CROSS-REFERENCE TO RELATED APPLICATIONS

This application claims priority from and the benefit of Korean Patent Application No. 10-2019-0152472, filed on Nov. 25, 2019, which is hereby incorporated by reference for all purposes as if fully set forth herein.

BACKGROUND

Field

Exemplary embodiments of the invention relate generally to an organic light emitting diode and, more specifically, to a plurality of hole transport layers having different refractive indexes.

Discussion of the Background

Various display devices such as televisions, mobile phones, tablet computers, navigation devices, and game consoles used in multimedia devices are being developed. These display devices use so-called self-luminescent display diodes in which a luminescent material including an organic compound, a quantum dot, or the like in the emission layer disposed between facing electrodes to emit light to implement a display.

In the application of an organic light emitting diode to a display device, it is required that the organic light emitting diode should have high luminous efficiency and a long service life, and the development on materials and a structure, for an organic light emitting diode, capable of stably attaining such characteristics is ongoing.

The above information disclosed in this Background section is only for understanding of the background of the inventive concepts, and, therefore, it may contain information that does not constitute prior art.

SUMMARY

The present disclosure provides an organic light emitting diode exhibiting excellent luminous efficiency.

Additional features of the inventive concepts will be set forth in the description with follows, and in part will be apparent from the description, or may be learned by practice of the inventive concepts.

According to one or more embodiments of the invention, an organic light emitting diode includes: a first electrode; a hole transport region disposed on the first electrode; an emission layer disposed on the hole transport region; an electron transport region disposed on upper portion of the emission layer; and a second electrode disposed on the electron transport region, wherein the hole transport region includes: a first hole transport layer having a first refractive index; and a second hole transport layer which has a second refractive index greater than the first refractive index and is disposed on the lower portion of the first hole transport layer.

The first hole transport layer may be directly disposed on the lower portion of the emission layer.

The ratio of the thickness $T_1$ of the first hole transport layer and the thickness $T_2$ of the second hole transport layer may satisfy the relationship of Expression 1 below:

$$1 \leq T_2/T_1 \leq 3. \quad \text{[Expression 1]}$$

The minimum value of the difference between the first refractive index and the second refractive index may be 0.2.

The first refractive index may be from 1.2 to 1.7, and the second refractive index may be from 1.7 to 1.9.

The first hole transport layer may include a fluorene compound represented by Formula 1 below:

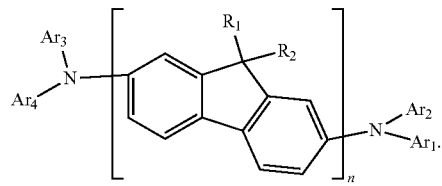

[Formula 1]

In Formula 1 above, $R_1$ and $R_2$ may be each independently a substituted or unsubstituted alkyl group having 1 to 30 carbon atoms, n may be an integer of 1 to 3, and $Ar_1$ to $Ar_4$ may be each independently a hydrogen atom, a deuterium atom, a halogen atom, a cyano group, a substituted or unsubstituted amino group, a substituted or unsubstituted aryl group having 6 to 60 carbon atoms, a substituted or unsubstituted heterocyclic group having 2 to 60 carbon atoms, or bonded to an adjacent group to form a ring.

$R_1$ and $R_2$ may be each independently a substituted or unsubstituted alkyl group having 1 to 10 carbon atoms.

The second hole transport layer may include a compound represented by Formula 2 below:

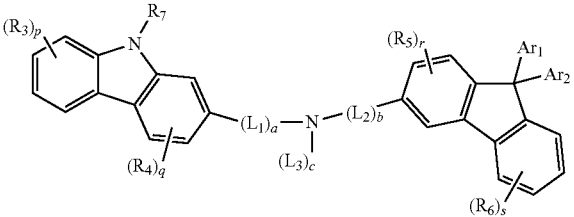

[Formula 2]

wherein, in Formula 2 above, $Ar_1$ and $Ar_2$ may be each independently a hydrogen atom, a deuterium atom, a halogen atom, a substituted or unsubstituted alkyl group having 1 to 30 carbon atoms, a substituted or unsubstituted aryl group having 6 to 30 carbon atoms, or bonded to an adjacent group to form a ring, a to c may be each independently an integer of 0 to 5, $L_1$ to $L_3$ may be each independently a substituted or unsubstituted cycloalkylene group having 3 to 10 ring-forming carbon atoms, a substituted or unsubstituted heterocycloalkylene group having 2 to 10 ring-forming carbon atoms, a substituted or unsubstituted cycloalkenylene group having 3 to 10 ring-forming carbon atoms, a substituted or unsubstituted arylene group having 6 to 30 ring-forming carbon atoms, or a substituted or unsubstituted heteroarylene group having 2 to 60 ring-forming carbon atoms, p and s may be each independently an integer of 0 to 3, q and r may be each independently an integer of 0 to 4, and $R_3$ to $R_7$ may be each independently a hydrogen atom, a deuterium atom, a halogen atom, a hydroxy group, a cyano group, a nitro group, an amino group, a substituted or unsubstituted silyl group, a substituted or unsubstituted oxy group, a substituted or unsubstituted alkyl group having 1 to 60 carbon atoms, a substituted or unsubstituted heterocycloalkyl group having 3 to 60 ring-forming carbon atoms, a substituted or unsubstituted aryl group having 6 to 60 ring-forming carbon atoms, or a substituted or unsubstituted heteroaryl group having 2 to 60 ring-forming carbon atoms.

The hole transport region may further include a third hole transport layer disposed on the lower portion of the second transport layer, wherein the third hole transport layer may include a p-dopant.

According to one or more embodiments of the invention, an organic light emitting diode includes a first electrode; a hole transport region disposed on the first electrode; an emission layer disposed on the hole transport region; an electron transport region disposed on the emission layer; and a second electrode disposed on the electron transport region, wherein the hole transport region includes a plurality of hole transport layers having different refractive indexes, and a layer among the plurality of hole transport layers which is directly disposed on the lower portion of the emission layer includes a fluorene compound represented by Formula 1 below:

[Formula 1]

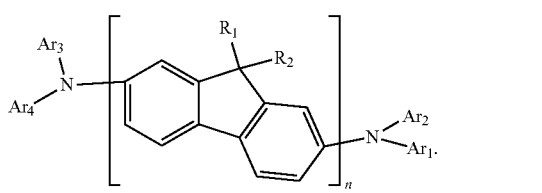

In Formula 1 above, $R_1$ and $R_2$ are each independently a substituted or unsubstituted alkyl group having 1 to 30 carbon atoms, n is an integer of 1 to 3, and $Ar_1$ to $Ar_4$ are each independently a hydrogen atom, a deuterium atom, a halogen atom, a cyano group, a substituted or unsubstituted amino group, a substituted or unsubstituted aryl group having 6 to 60 carbon atoms, a substituted or unsubstituted heterocyclic group having 2 to 60 carbon atoms, or are bonded to an adjacent group to form a ring.

The hole transport region may include a first hole transport layer having a first refractive index; and a second hole transport layer which has a second refractive index greater than the first refractive index and is disposed on the lower portion of the first hole transport layer.

It is to be understood that both the foregoing general description and the following detailed description are exemplary and explanatory and are intended to provide further explanation of the invention as claimed.

BRIEF DESCRIPTION OF THE FIGURES

The accompanying drawings are included to provide a further understanding of the inventive concepts, and are incorporated in and constitute a part of this specification. The drawings illustrate exemplary embodiments of the inventive concepts and, together with the description, serve to explain principles of the inventive concepts.

DETAILED DESCRIPTION

Figure 1:
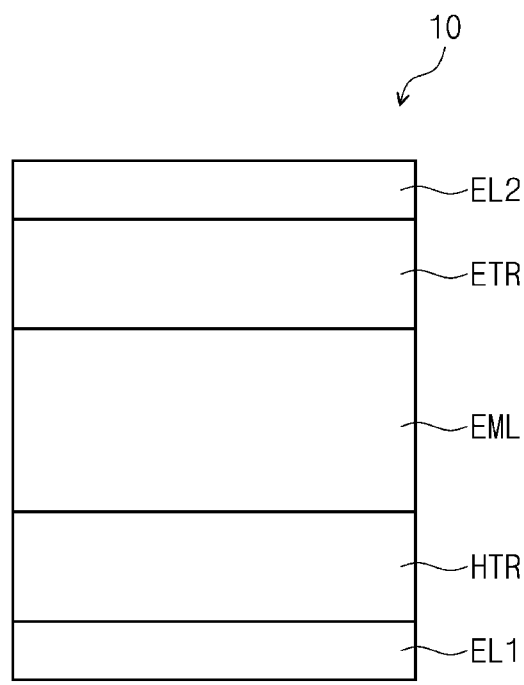
FIG. 1 is a cross-sectional view schematically illustrating an organic light emitting diode according to an embodiment of the inventive concepts.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In the accompanying figures, the size and relative sizes of layers, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. Thus, the regions illustrated in the drawings are schematic in nature and their shapes are not intended to illustrate the actual shape of a region of a device and are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Hereinafter, an organic light emitting diode to an embodiment of the inventive concepts will be described with reference to the drawings.

Figure 2:
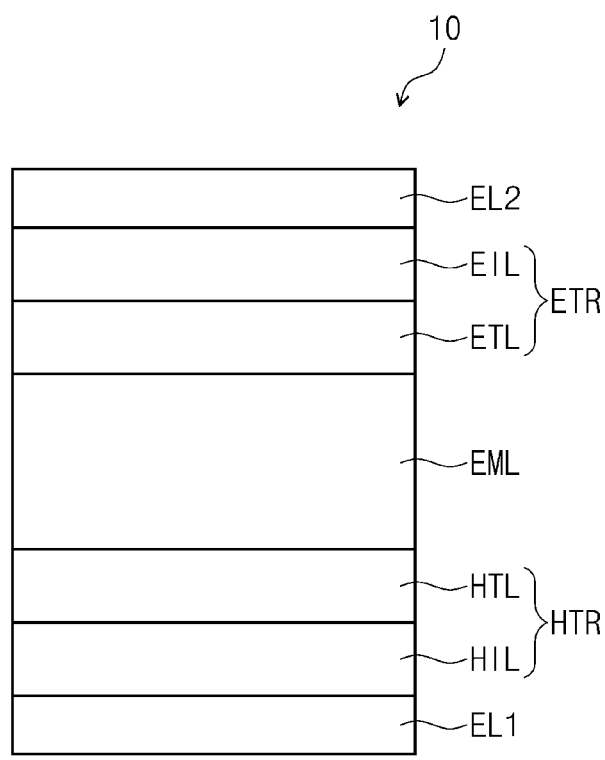
FIG. 2 is a cross-sectional view schematically illustrating an organic light emitting diode according to an embodiment of the inventive concepts.
Figure 3:
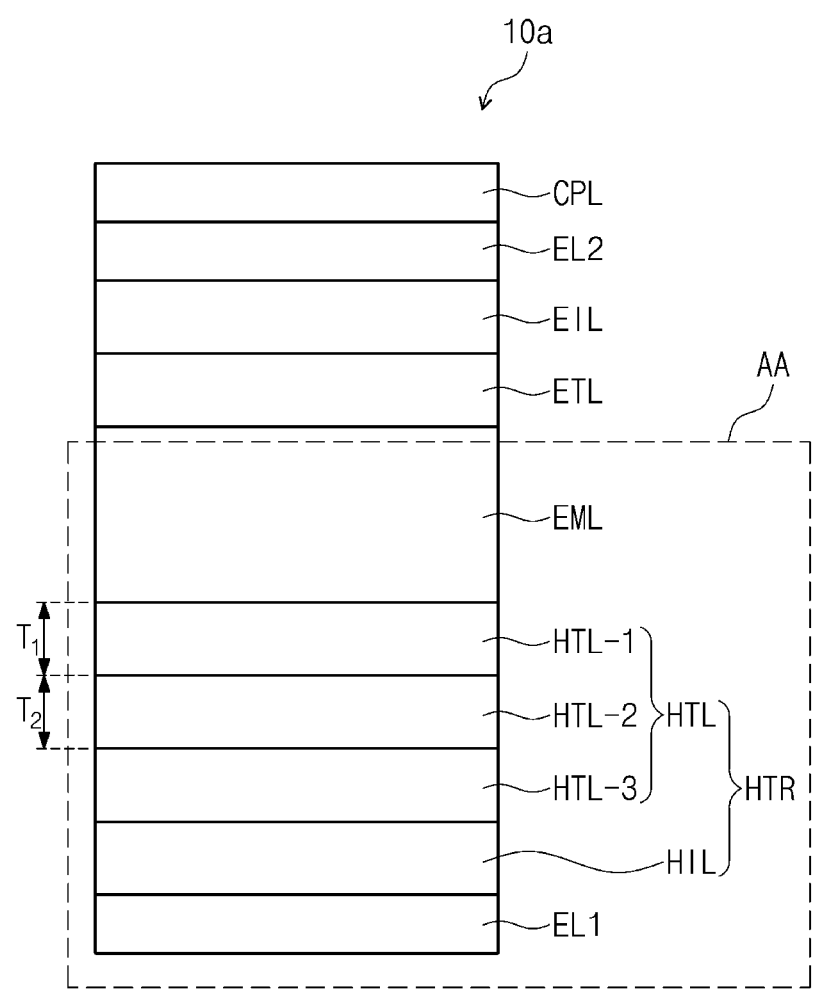
FIG. 3 is a cross-sectional view schematically illustrating an organic light emitting diode according to an embodiment of the inventive concepts.

FIGS. 1, 2, and 3 are cross-sectional views schematically illustrating an organic light emitting diode according to one or more embodiments of the inventive concepts. Referring to FIGS. 1, 2, and 3, in an organic light emitting diode 10 or 10a according to an embodiment, a first electrode EL1 and a second electrode EL2 are disposed to face each other, and a hole transport region HTR, an emission layer EML, and an electron transport region ETR may be disposed between the first electrode EL1 and the second electrode EL2. In addition, the organic light emitting diode 10a of an embodiment may include a capping layer CPL disposed on the second electrode EL2.

Meanwhile, compared to FIG. 1, FIG. 2 illustrates a cross-sectional view of an organic light emitting diode 10 of an embodiment, in which a hole transport region HTR includes a hole injection layer HIL and a hole transport layer HTL, and an electron transport region ETR includes an electron injection layer EIL and an electron transport layer ETL. In addition, FIG. 3 illustrates a cross-sectional view of an organic light emitting diode 10a of an embodiment in which a hole transport region HTR includes a first hole transport layer HTL-1 to a third hole transport layer HTL-3 and which includes a capping layer CPL disposed on the second electrode EL2.

The organic light emitting diode 10 of an embodiment may include the first electrode EL1, the hole transport region HTR, the emission layer EML, the electron transport region ETR, and the second electrode EL2 that are sequentially stacked. According to an embodiment, the hole transport region HTR may include a plurality of hole transport layers HTL-1, HTL-2, and HTL-3 having different refractive indexes. The plurality of hole transport layers may include a first hole transport layer HTL-1 having a first refractive index; and a second hole transport layer HTL-2 which has a second refractive index greater than the first refractive index and is disposed on the lower portion of the first hole transport layer HTL-1. A layer, among the plurality of hole transport layers, which is adjacent to the emission layer EML may include a fluorene compound of an embodiment, which will be described later.

In the organic light emitting diode 10 of an embodiment, the first electrode EL1 has conductivity. The first electrode EL1 may be formed of a metal alloy or a conductive compound. The first electrode EL1 may be an anode. In addition, the first electrode EL1 may be a pixel electrode. The first electrode EL1 may be a reflective electrode. When the first electrode EL1 is the reflective electrode, the first electrode EL1 may include Ag, Mg Cu, Al, Pt, Pd, Au, Ni, Nd, Ir, Cr, Li, Ca, LiF/Ca, LiF/Al, Mo, Ti, a compound thereof or a mixture thereof (e.g., a mixture of Ag and Mg). Alternatively, the first electrode EL1 may have a multilayer structure including a reflective layer or a transflective layer formed of the above-described materials, and a transparent conductive layer formed of ITO (indium tin oxide), IZO (indium zinc oxide), ZnO (zinc oxide), ITZO (indium tin zinc oxide), etc. For example, the first electrode EL1 may have a three-layer structure of ITO/Ag/ITO, but is not limited thereto. The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include a plurality of hole transport layers HTL-1, HTL-2, and HTL-3 having different refractive indexes, and may further include at least one of a hole buffer layer (not shown) or an electron blocking layer (not shown). The thickness of the hole transport region HTR may be, for example, from about 1,000 Å to about 1,800 Å.

The hole transport region HTR may have a multilayer structure including a plurality of layers formed of a plurality of different materials.

For example, the hole transport region HTR may have a multilayer structure formed of a hole injection layer HIL and a hole transport layer HTL, and may have a multilayer structure formed of a plurality of hole injection materials and a plurality of hole transport materials. In addition, the hole transport region HTR may have a structure in which a hole injection layer HIL/hole transport layer HTL, a hole injection layer HIL/hole transport layer HTL/hole buffer layer (not shown), a hole injection layer HIL/hole transport layer HTL/electron blocking layer (not shown) are stacked in order from the first electrode EL1, but an embodiment is not limited thereto.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N-diphenyl-N,N-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4'-tris{N-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate)

(PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f:2',3'-h]quinoxaline-2,3,6,7,10,11-hexacarbonitrile (HAT-CN), etc.

In the description, the term "substituted or unsubstituted" may mean substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the substituents exemplified above may be substituted or unsubstituted. For example, a biphenyl group may be interpreted as an aryl group or a phenyl group substituted with a phenyl group.

In the description, the alkyl group may be linear or branched. The number of carbons in the alkyl group is 1 to 50, 1 to 30, 1 to 20, 1 to 10, or 1 to 6. Examples of the alkyl group may include, but are not limited to, methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc.

In the description, examples of the halogen atom may include a fluorine atom, a chlorine atom, a bromine atom, and an iodine atom.

In the description, the number of carbon atoms in an amino group is not specifically limited, but may be 1 to 30. The amino group may include an alkyl amino group, an aryl amino group, or a heteroaryl amino group. Examples of the amino group include a methylamino group, a dimethylamino group, a phenylamino group, a diphenylamino group, a naphthylamino group, a 9-methyl-anthracenylamino group, a triphenylamino group, etc., but are not limited thereto.

In the description, an aryl group means any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include, but are not limited to, a phenyl group, a naphthyl group, a fluorenyl group, an anthracenyl group, a phenanthryl group, a biphenyl group, a terphenyl group, a quaterphenyl group, a quinqphenyl group, a sexiphenyl group, a triphenylenyl group, a pyrenyl group, a benzofluoranthenyl group, a chrysenyl group, etc.

In the description, the heterocyclic group may include at least one of B, O, N, P, Si or S as a hetero atom. When the heterocyclic group contains two or more hetero atoms, the two or more hetero atoms may be the same as or different from each other. The heterocyclic group may be a monocyclic heterocyclic group or a polycyclic heterocyclic group, and includes a heteroaryl group. The number of ring-forming carbon atoms in in the heterocyclic group may be 2 to 60, 2 to 30, or 2 to 20. Examples of the heteroaryl group may include oxirane, tyran, pyrrolidine, piperidine, tetrahydrofuran, tetrahydrothiophene, thian, tetrahydropyran, 1,4-dioxane, thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophenyl, thienothiophene, benzofuranyl, phenanthroline, thiazole, isooxazole, oxazole, oxadiazole, thiadiazole, phenothiazine, dibenzosilole, dibenzofuran, etc., but are not limited thereto.

In the description, an oxy group may an alkoxy group and an aryl oxy group. The alkoxy group may be a linear, branched or cyclic chain. The number of carbon atoms in the alkoxy group and the aryloxy group is not particularly limited, but for example, it may be 1 to 60 or 1 to 30. Examples of an oxy group include methoxy, ethoxy, n-propoxy, isopropoxy, butoxy, pentyloxy, hexyloxy, octyloxy, nonyloxy, decyloxy, benzyloxy, etc., but are not limited thereto.

The hole transport region HTR of an embodiment may include a first hole transport layer HTL-1 having a first refractive index, and a second hole transport layer HTL-2 which has a second refractive index greater than the first refractive index and is disposed on the lower portion of the first hole transport layer HTL-1. In addition, the hole transport region HTR may further include a third hole transport layer HTL-3 disposed on the lower portion of the second hole transport layer HTL-2. That is, the first hole transport layer HTL-1 may be disposed between the emission layer EML and the second hole transport layer HTL-2. The first hole transport layer HTL-1 of an embodiment may be directly disposed on the lower portion of the emission layer EML and include a fluorene compound represented by Formula 1 below:

[Formula 1]

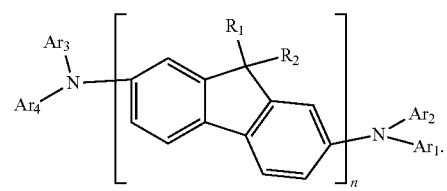

In Formula 1, $R_1$ and $R_2$ may be each independently a substituted or unsubstituted alkyl group having 1 to 30 carbon atoms, and n may be an integer of 1 to 3. For example, n may be 2.

$Ar_1$ to $Ar_4$ may be each independently a hydrogen atom, a deuterium atom, a halogen atom, a cyano group, a substituted or unsubstituted amino group, a substituted or unsubstituted aryl group having 6 to 60 carbon atoms, a substituted or unsubstituted heterocyclic group having 2 to 60 carbon atoms, or bonded to an adjacent group to form a ring.

$R_1$ and $R_2$ may be each independently a substituted or unsubstituted alkyl group having 1 to 10 carbon atoms, and linear or branched. $Ar_1$ to $Ar_4$ may be all the same or at least one thereof may be different from the others. For example, $R_1$ and $R_2$ may be a hexyl group. $Ar_1$ to $Ar_4$ may be all carbazole groups or biphenyl groups.

A fluorene compound of an embodiment may be any one among the compounds represented by Compound Group 1 below. The organic light emitting diode 10, 10a of an embodiment may include at least one fluorene compound among the compounds represented by Compound Group 1 in the first hole transport layer HTL-1.

[Compound Group 1]

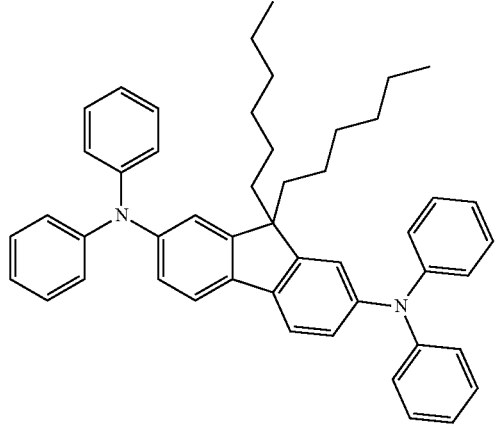

1

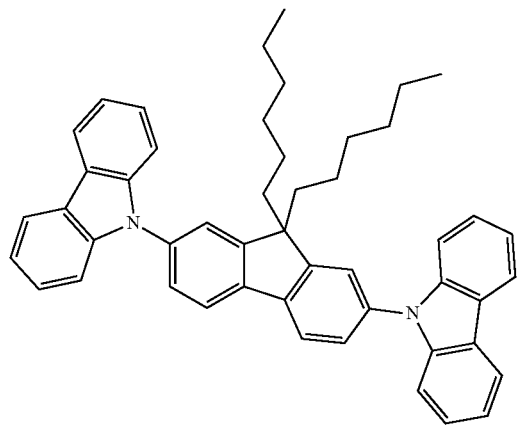

2

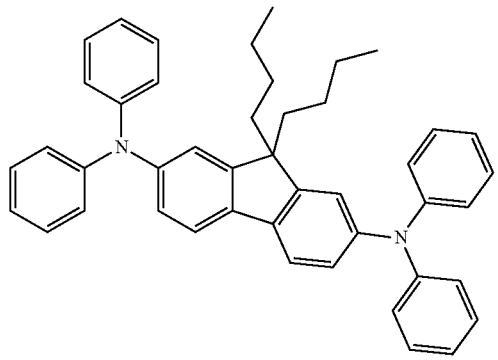

3

4
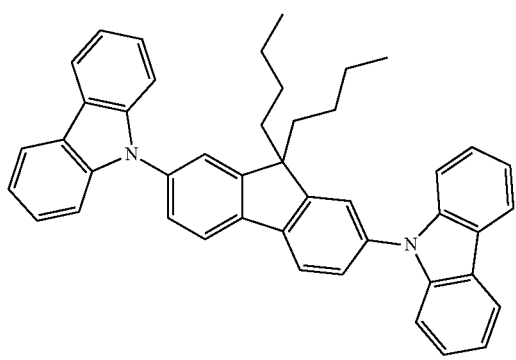
5
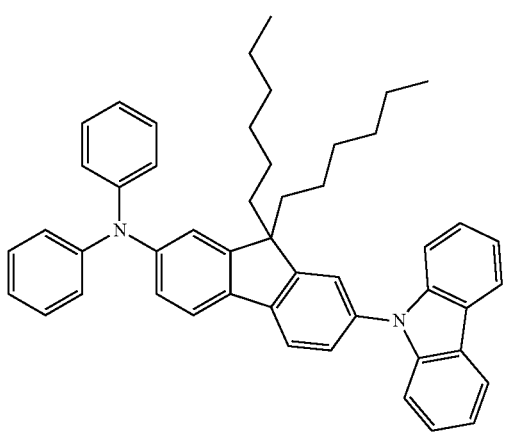
6
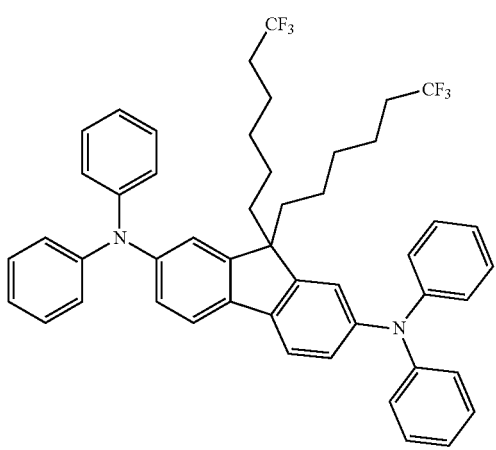
7
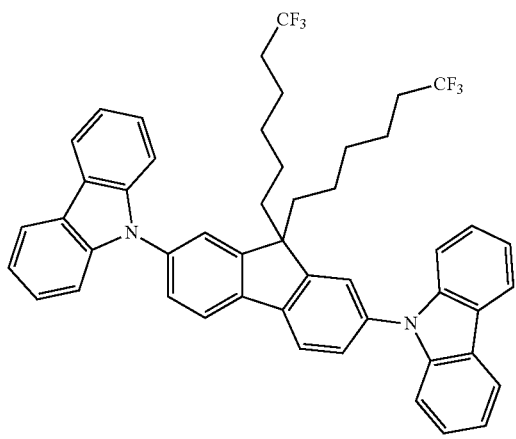

-continued

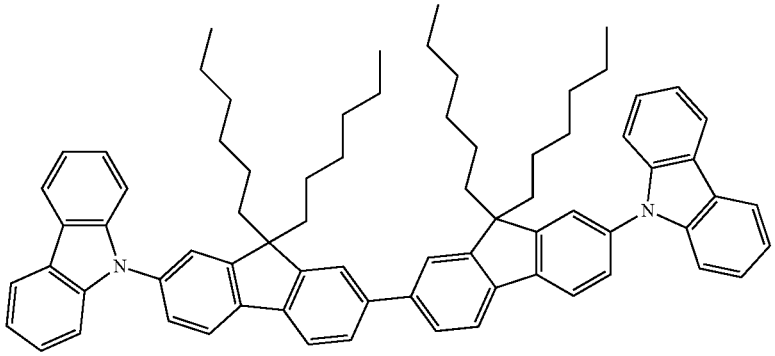

8

Meanwhile, acrylic, polyimide, polyamide, tis(8-hydroxyquinolinato)aluminium (Alq3), etc. may be further used as a material for the first hole transport layer HTL-1, but an embodiment is not limited thereto.

According to an embodiment, the second hole transport layer HTL-2 may include a compound represented by Formula 2 below:

[Formula 2]

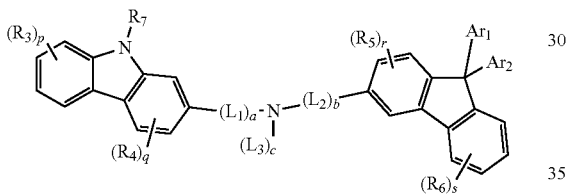

In Formula 2, $Ar_1$ and $Ar_2$ may be a hydrogen atom, a deuterium atom, a halogen atom, a substituted or unsubstituted alkyl group having 1 to 30 carbon atoms, a substituted or unsubstituted aryl group having 6 to 30 carbon atoms, or bonded to an adjacent group to form a ring, a to c may be each independently an integer of 0 to 5. $L_1$ to $L_3$ may be each independently a substituted or unsubstituted cycloalkylene group having 3 to 10 ring-forming carbon atoms, a substituted or unsubstituted heterocycloalkylene group having 2 to 10 ring-forming carbon atoms, a substituted or unsubstituted cycloalkenylene group having 3 to 10 ring-forming carbon atoms, a substituted or unsubstituted arylene group having 6 to 30 ring-forming carbon atoms, or a substituted or unsubstituted heteroarylene group having 2 to 60 ring-forming carbon atoms. For example, when a and b is 0, c may be 1, and $L_3$ may be an arylene group or a heteroarylene group.

p and s may be each independently an integer of 0 to 3, and q and r may be each independently an integer of 0 to 4. For example, when p to s are an integer of 2 or more, a plurality of $R_3$'s to $R_6$'s may be all the same or different from each other.

$R_3$ to $R_7$ may be each independently a hydrogen atom, a deuterium atom, a halogen atom, a hydroxy group, a cyano group, a nitro group, an amino group, a substituted or unsubstituted silyl group, a substituted or unsubstituted oxy group, a substituted or unsubstituted alkyl group having 1 to 60 carbon atoms, a substituted or unsubstituted heterocycloalkyl group having 3 to 60 ring-forming carbon atoms, a substituted or unsubstituted aryl group having 6 to 60 ring-forming carbon atoms, or a substituted or unsubstituted heteroaryl group having 2 to 60 ring-forming carbon atoms.

The compound of an embodiment represented by Formula 2 may be any one among the compounds represented by Compound Group 2. The organic light emitting diode 10, 10a of an embodiment may include at least one compound among the compounds represented by Compound Group 2 in the second hole transport layer HTL-2.

[Compound Group 2]

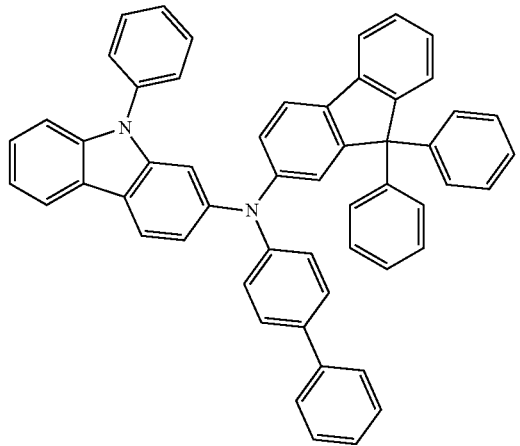

9

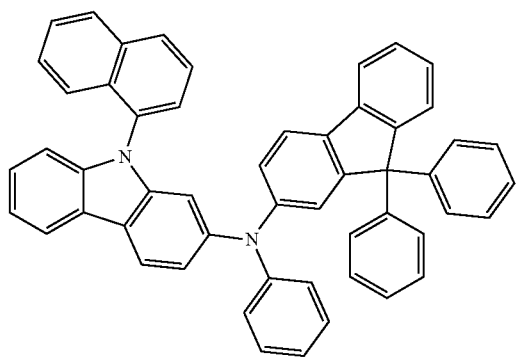

10

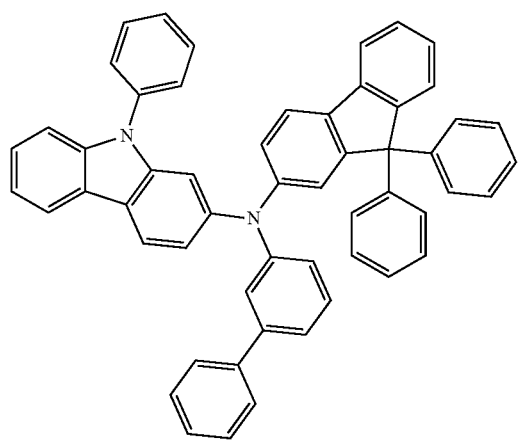
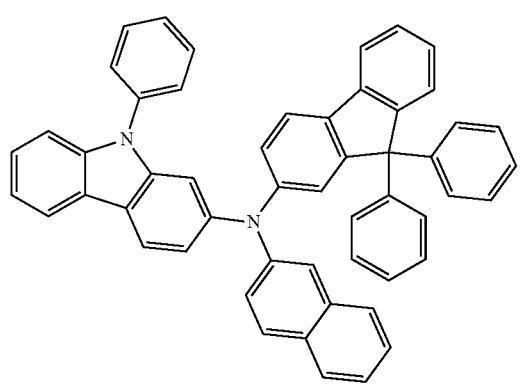
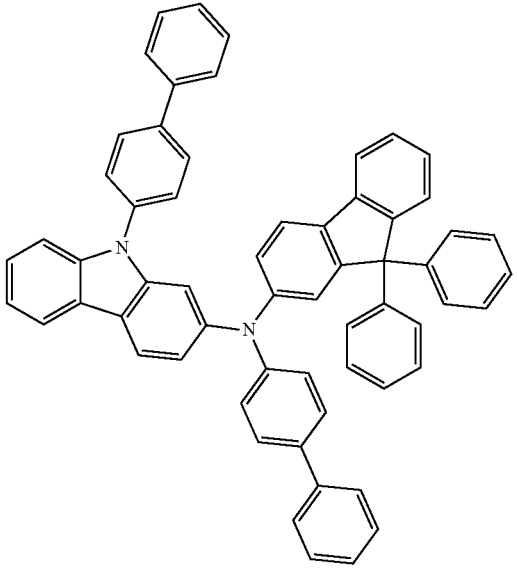
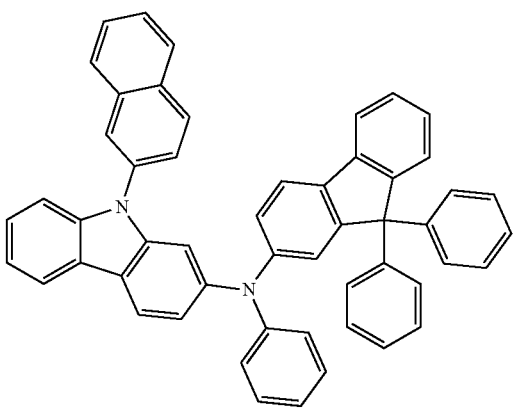
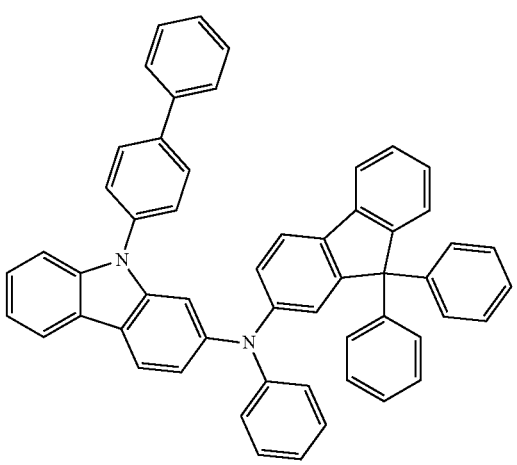

18
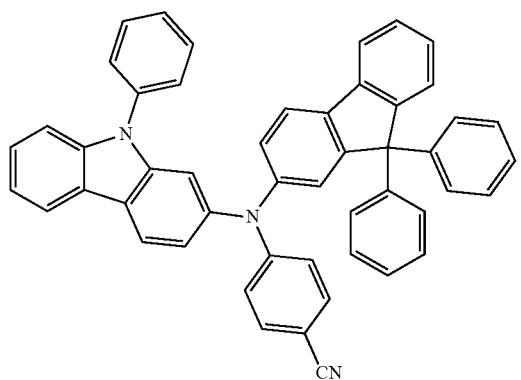
19
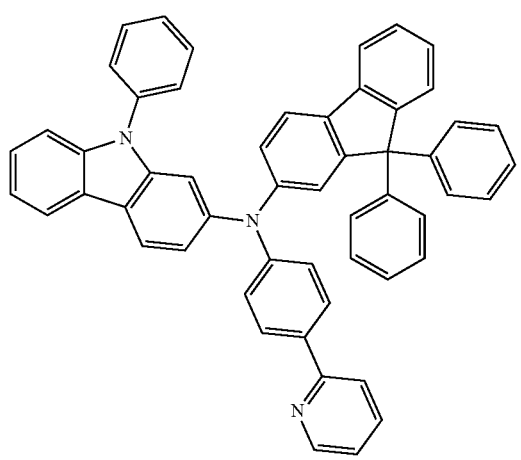
20
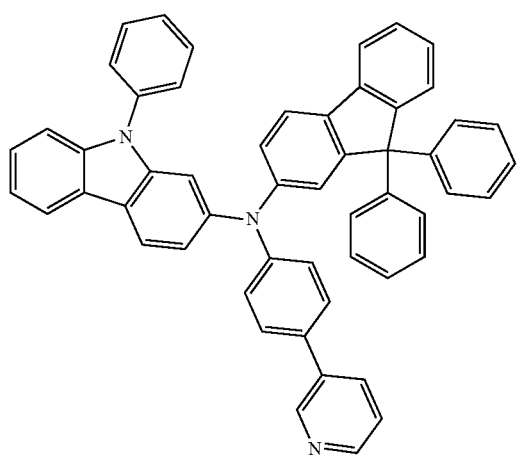
21
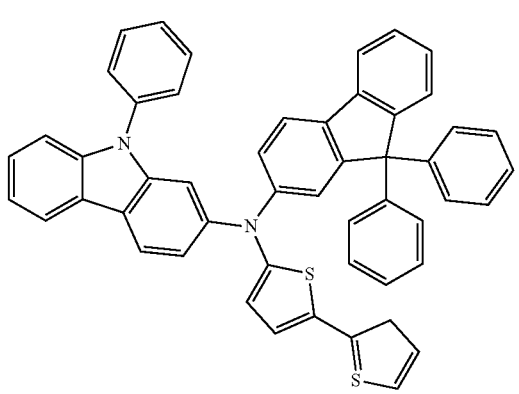
22
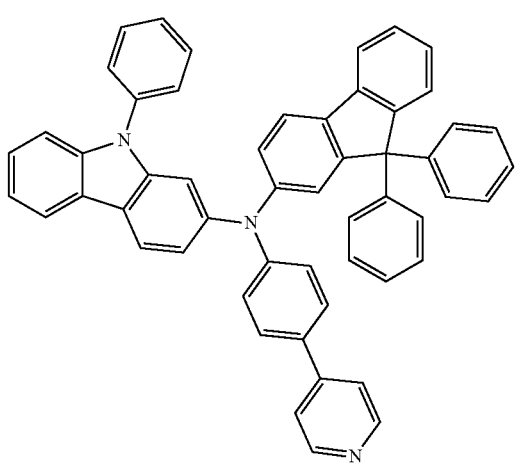
23
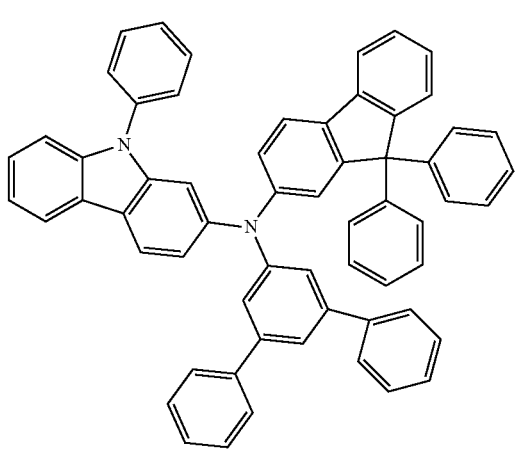

-continued
24
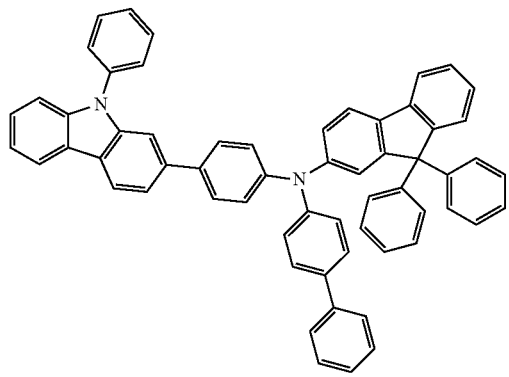
25
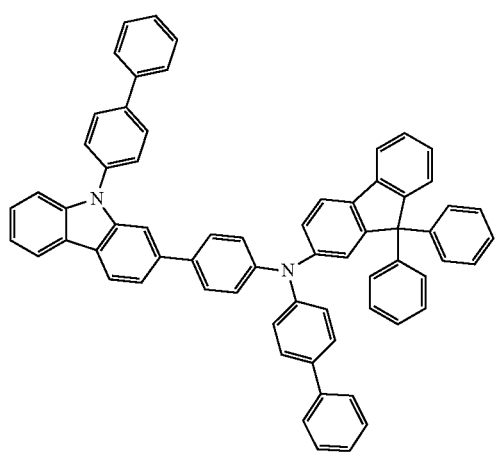
26
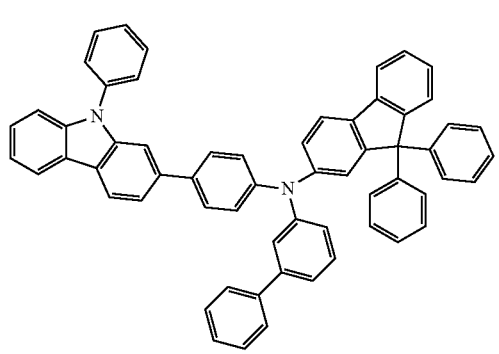
27
-continued
28
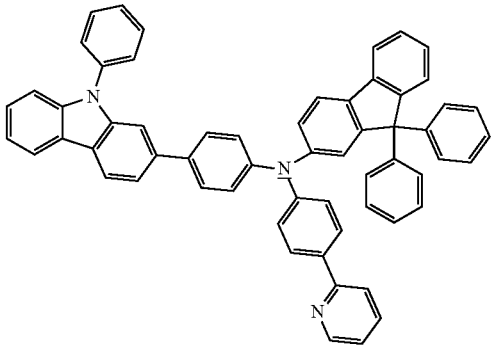
29
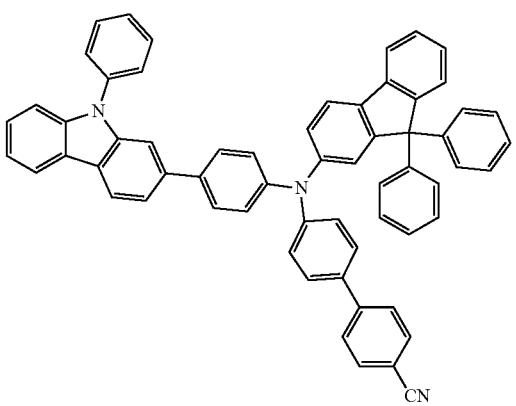
30
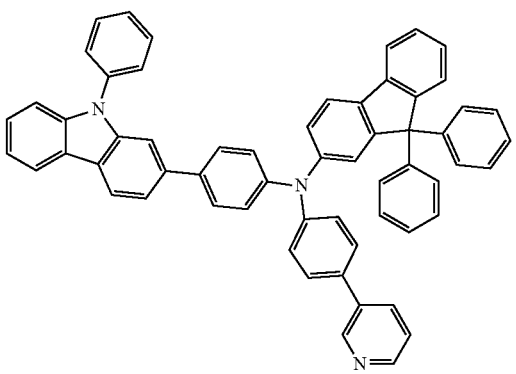
31
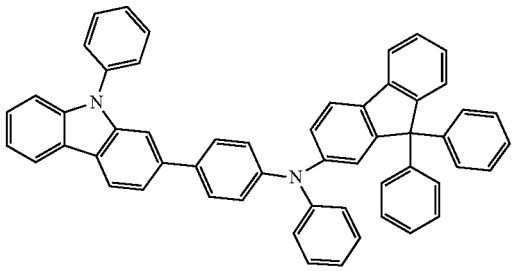

32
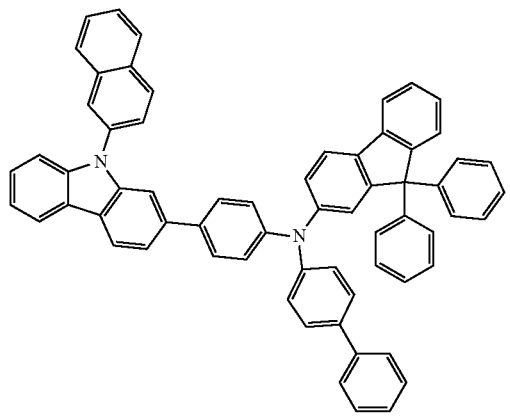
33
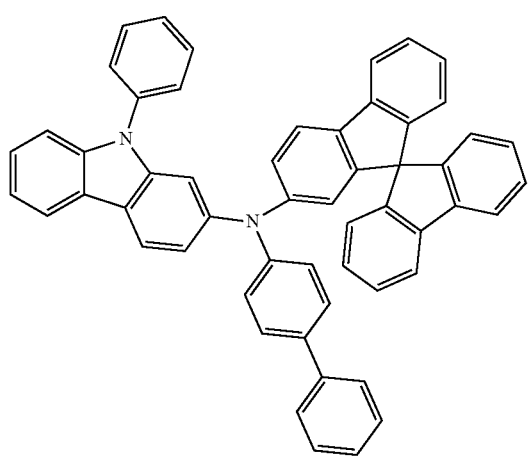
34
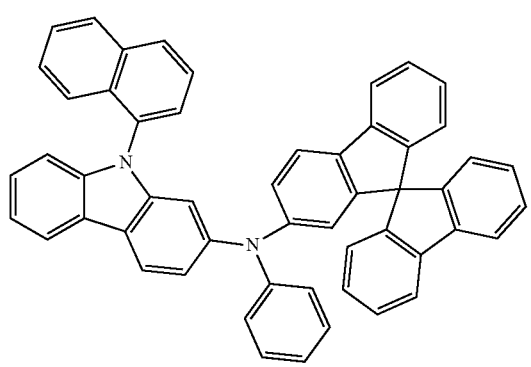
35
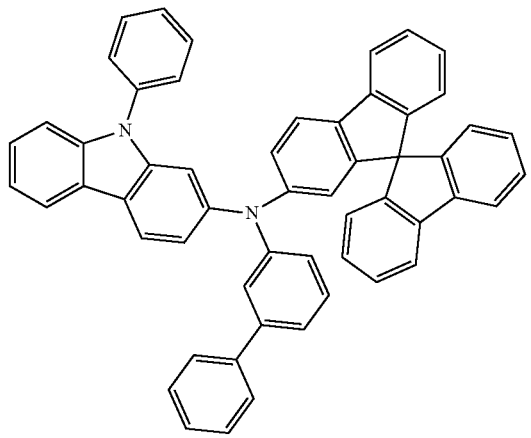
36
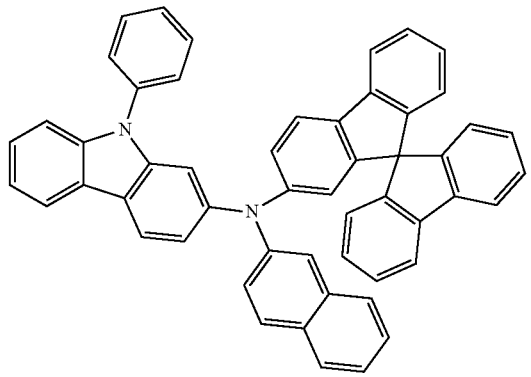
37
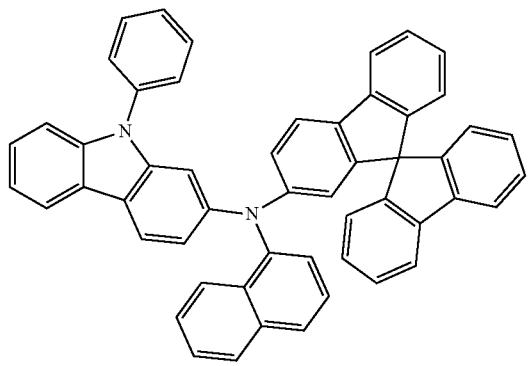
38
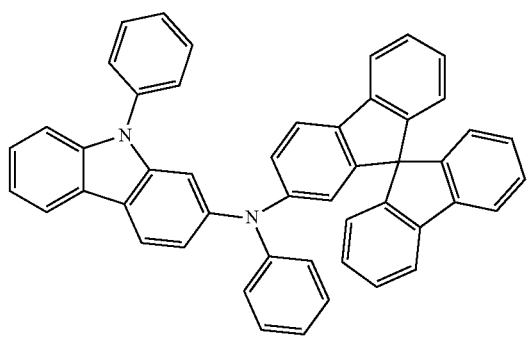

39
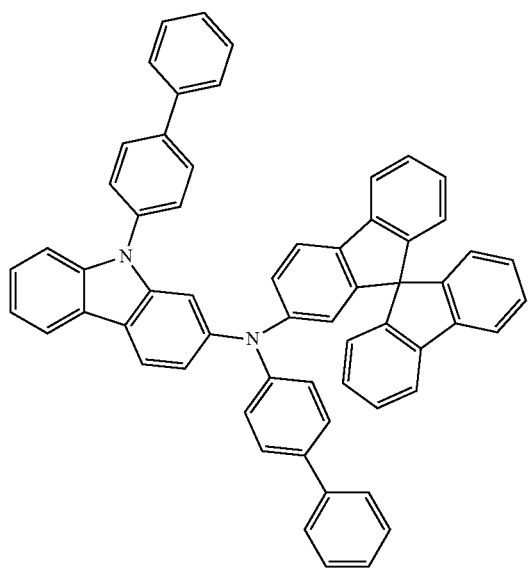
40
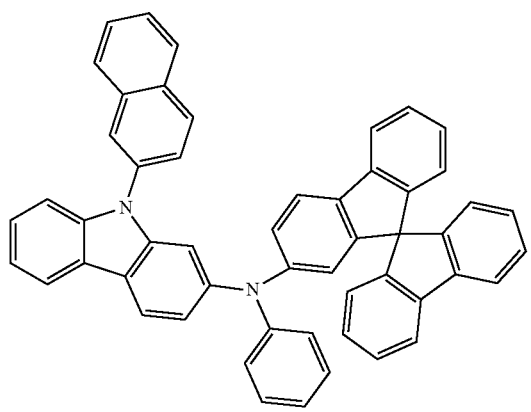
41
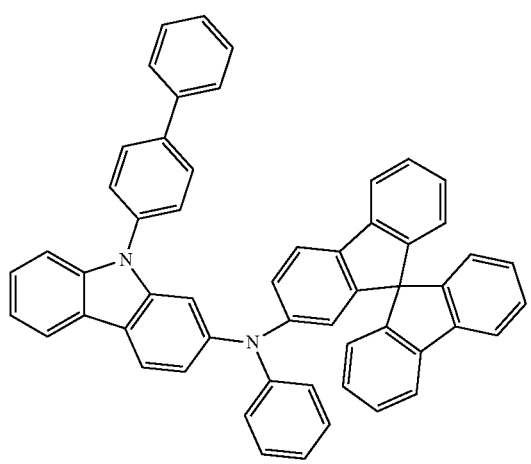
42
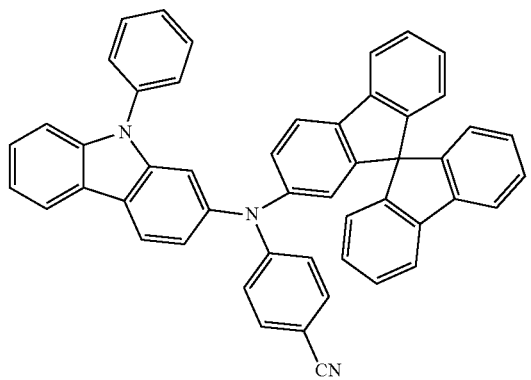
43
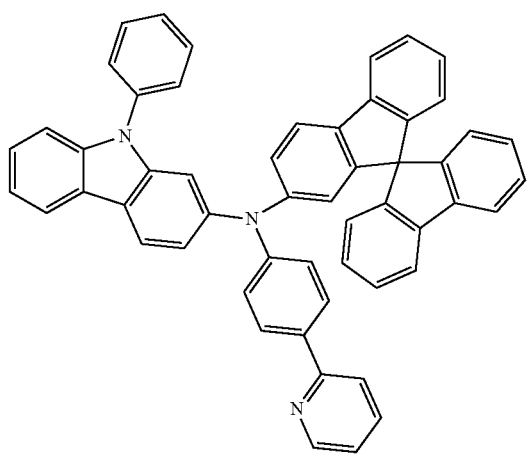
44
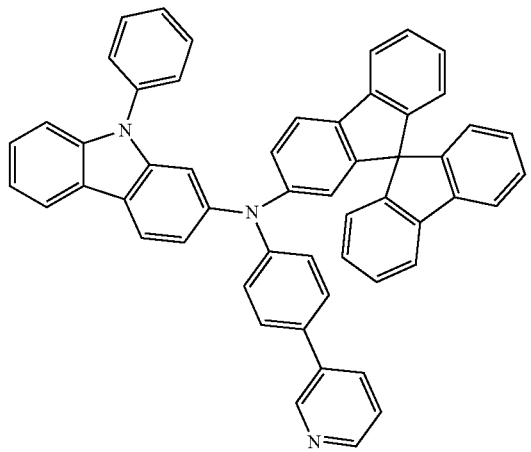

45
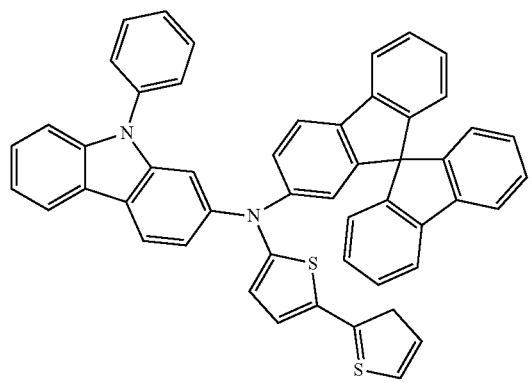
46
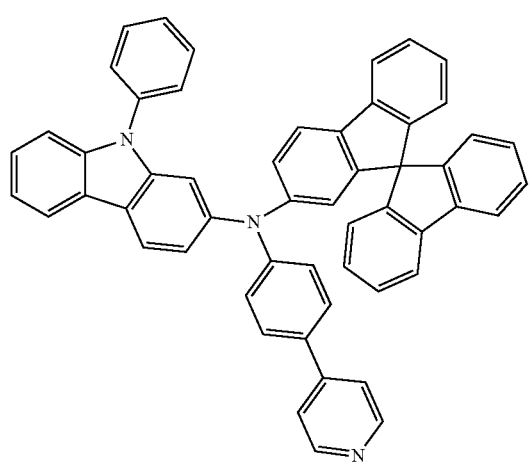
47
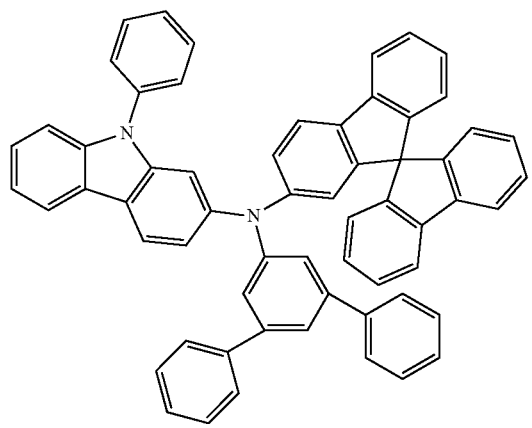
48
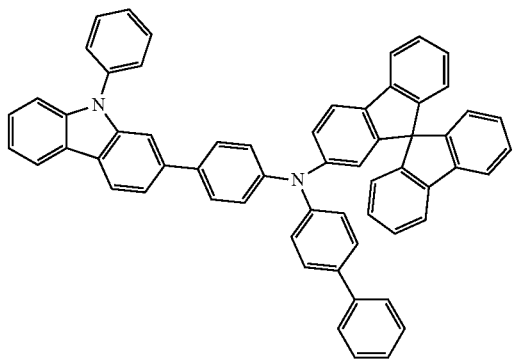
49
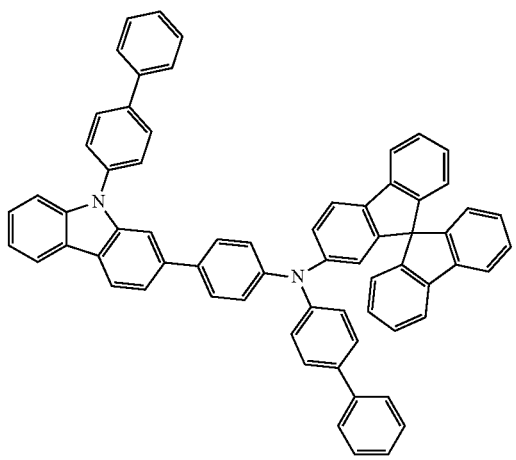
50
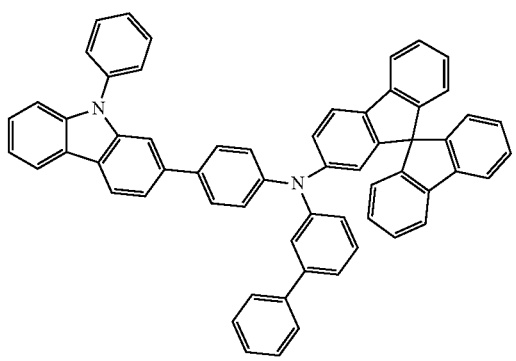
51
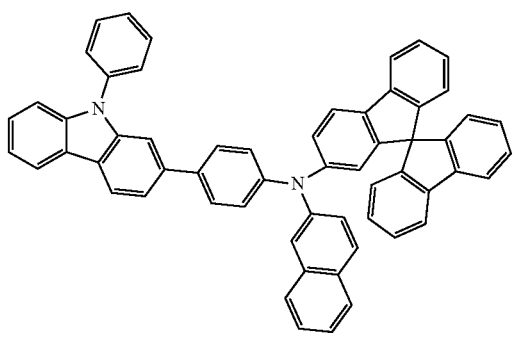

52
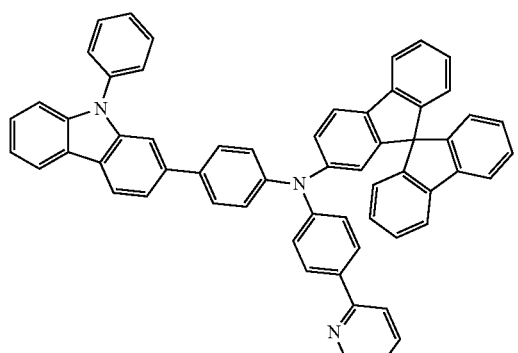
53
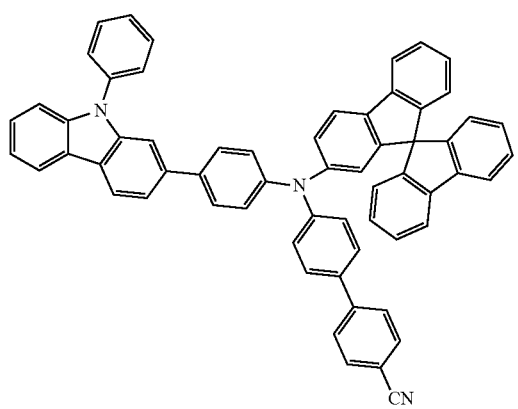
54
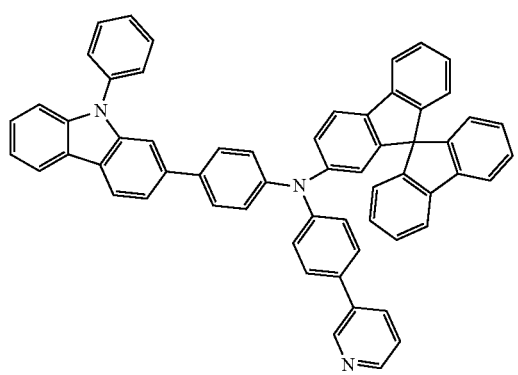
55
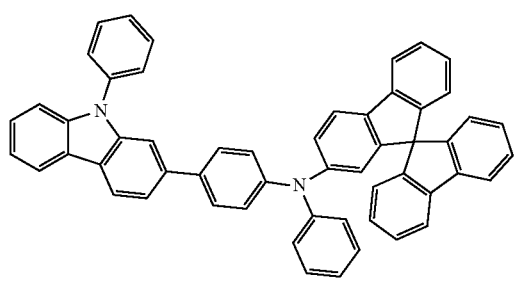
56
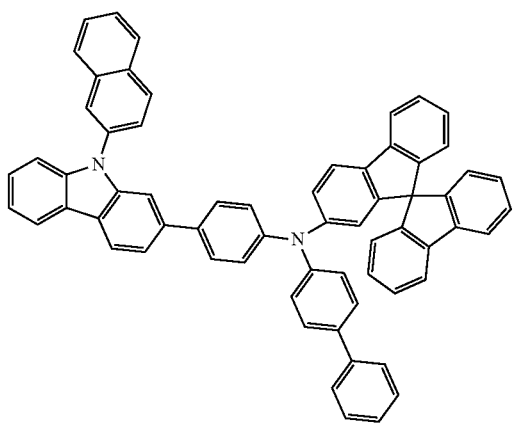
57
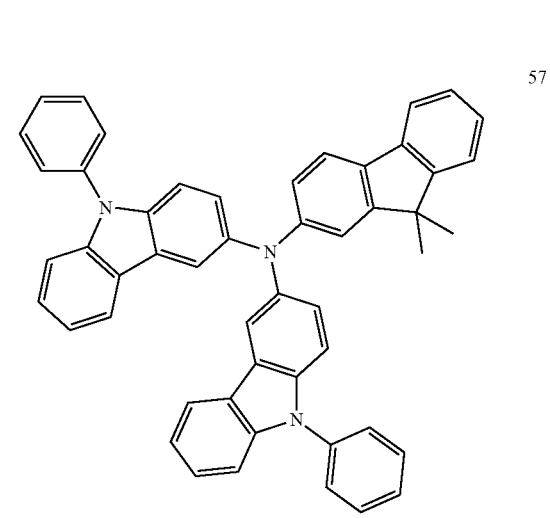
58
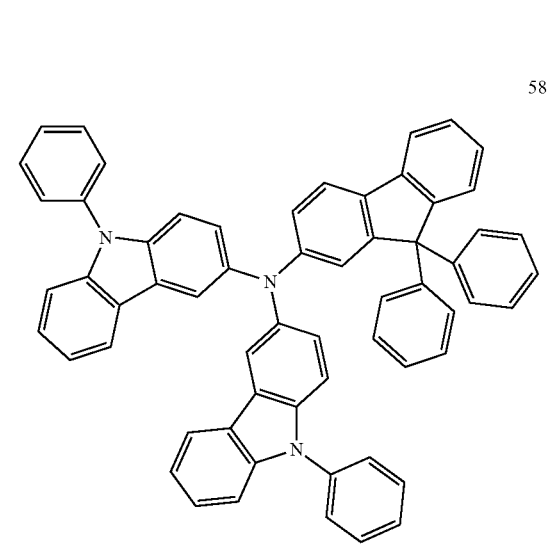

59
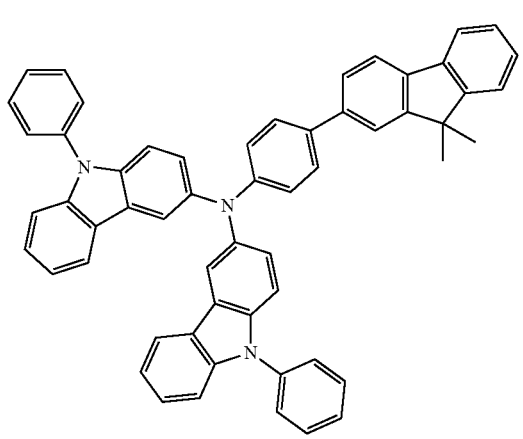
60
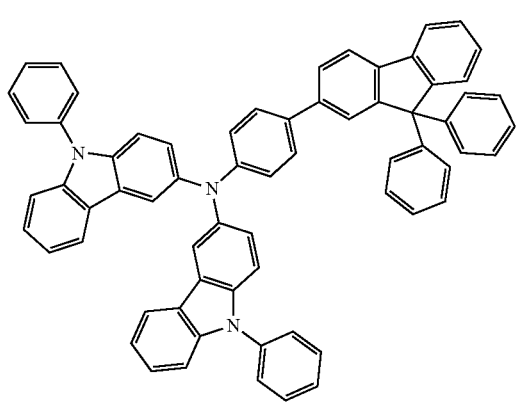
61
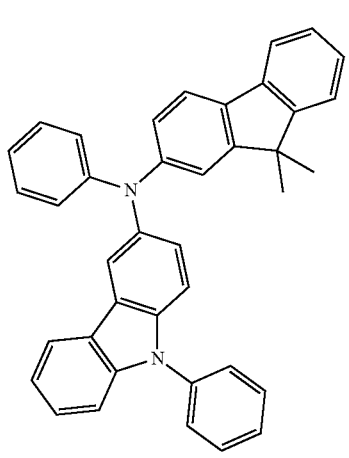
62
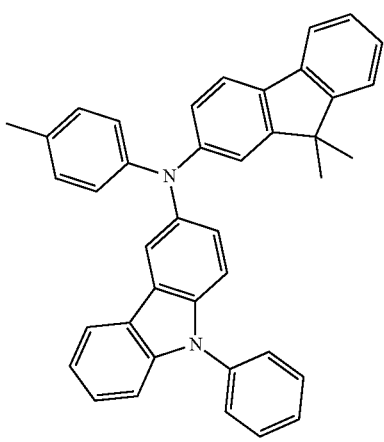
63
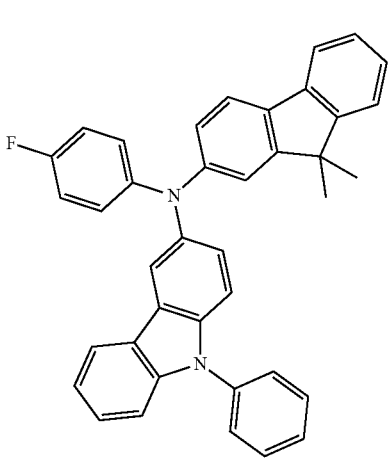
64
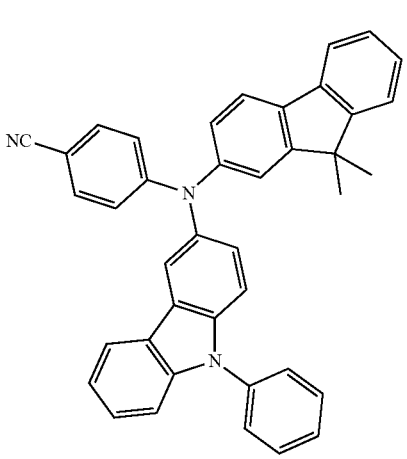

31
-continued
65
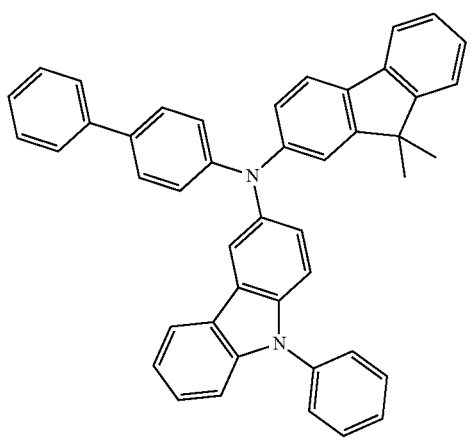
66
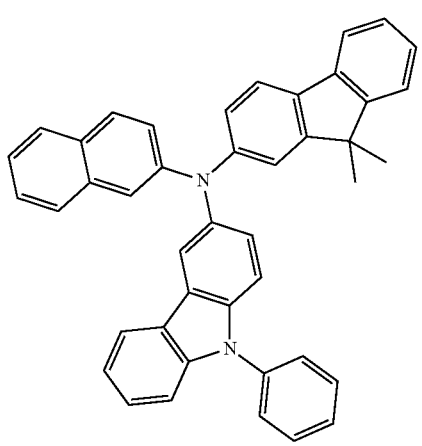
67
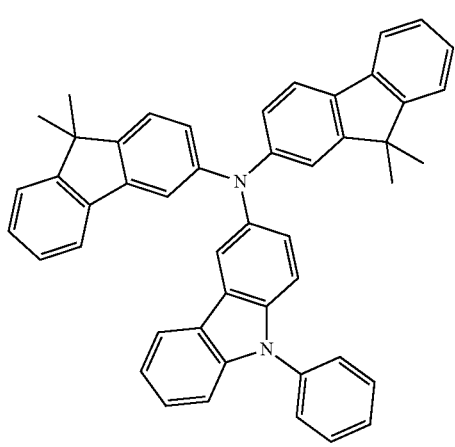
32
-continued
68
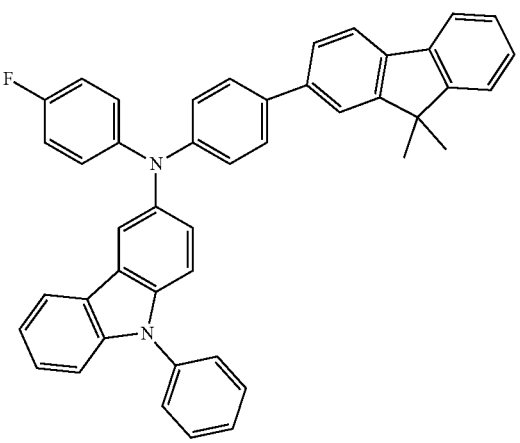
69
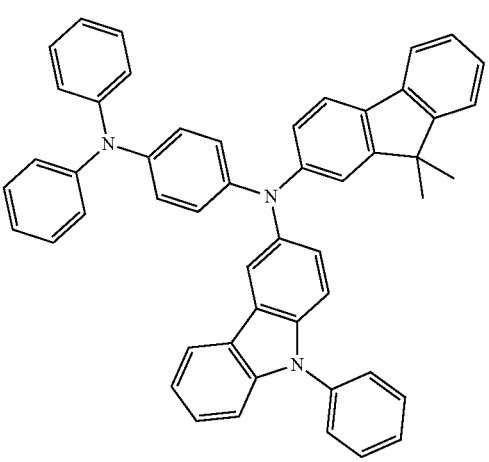
70
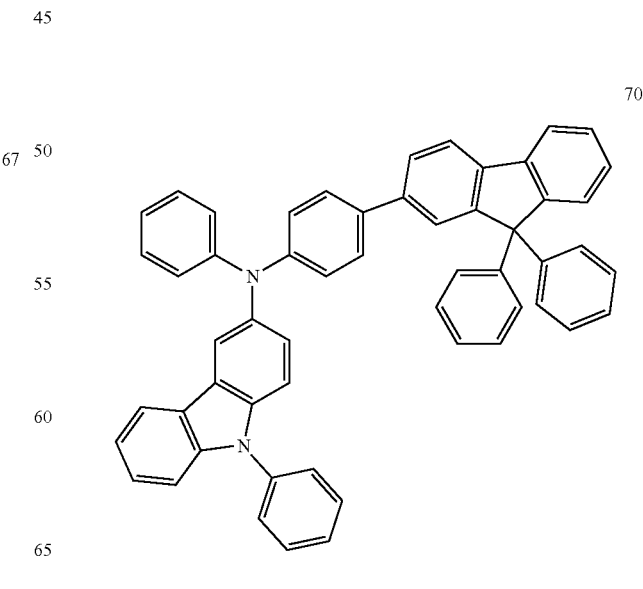

-continued
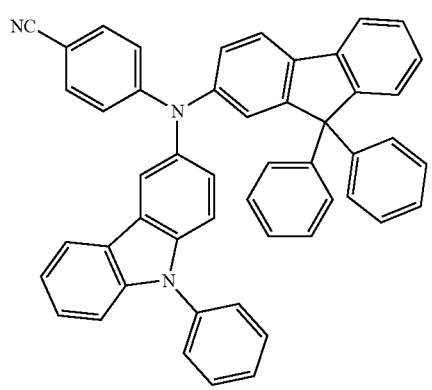
71
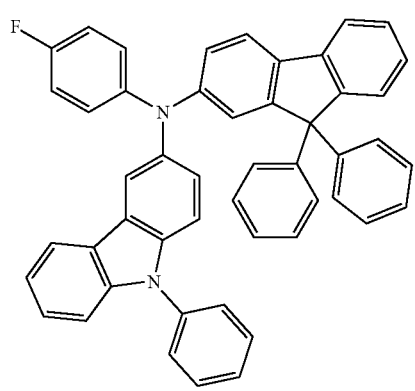
72
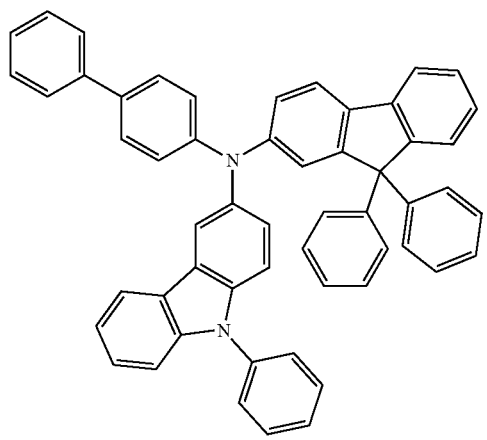
73
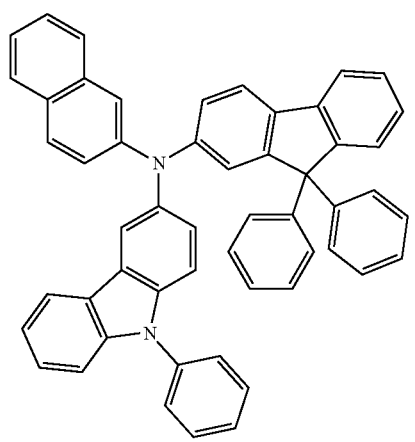
74
-continued
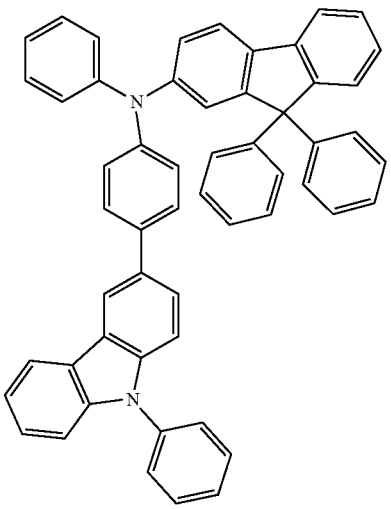
75
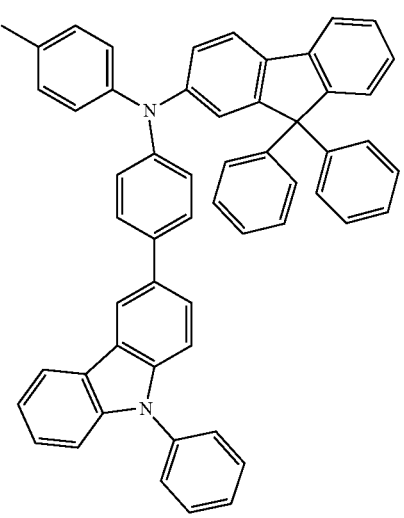
76
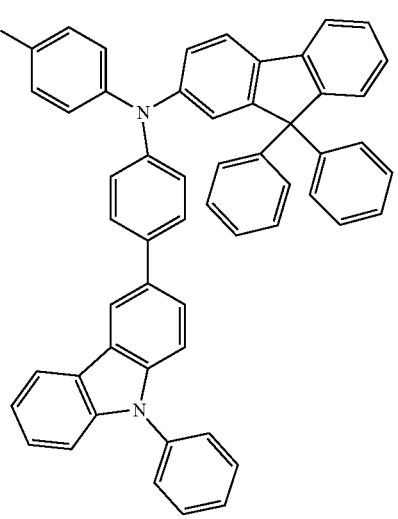
77

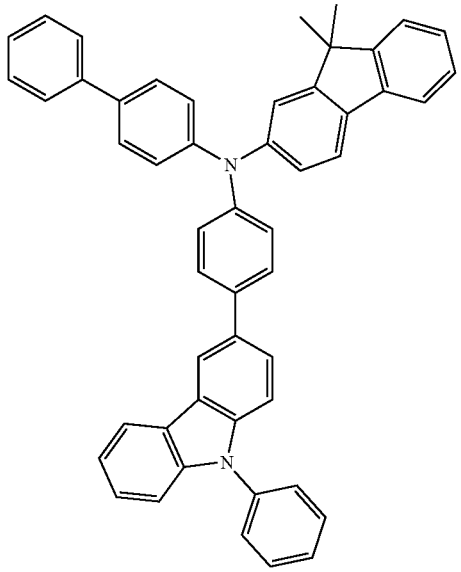

According to an embodiment, the difference between the first fractive index and the second fractive index may be 0.2 or more. The first refractive index may be from 1.2 to 1.7. The second refractive index greater than the first refractive index may be from 1.7 to 1.9. For example, the refractive index of the first hole transport layer HTL-1 may be 1.6, and the refractive index of the second hole transport layer HTL-2 may be 1.9. However, embodiments are not limited thereto.

The thickness $T_1$ of the first hole transport layer HTL-1 and the thickness $T_2$ of the second hole transport layer HTL-2 may satisfy the relationship of Expression 1.

$$1 \leq T_2/T_1 \leq 3 \quad \text{[Expression 1]}$$

The thickness $T_2$ of the second hole transport layer HTL-2 may be the same as that of the first hole transport layer HTL-1 or up to three times the thickness $T_1$ of the first hole transport layer HTL-1. For example, the thickness of the first hole transport layer HTL-1 may be from about 100 Å to about 3,200 Å, and the thickness of the second hole transport layer HTL-2 may be from about 100 Å to about 1,600 Å.

Meanwhile, the second hole transport layer HTL-2 may further include carbazole derivatives such as N-phenyl carbazole and polyvinyl carbazole, fluorene derivatives, N,N'-bis(3-methylphenyl)-N,N-diphenyl-[1,1-biphenyl]-4,4'-diamine (TPD), triphenylamine derivatives such as 4,4',4''-tris(N-carbazolyl)triphenylamine (TCTA), N,N'-di(naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. When the thicknesses of the hole transport region HTR, the hole injection layer HIL, and the hole transport layer HTL satisfy the above-described ranges, satisfactory hole transport characteristics may be achieved without a substantial increase in driving voltage.

Meanwhile, the third hole transport layer HTL-3 may be a layer including Compound 2 described above and a p-dopant. For example, the p-dopant may be Compound 3.

[Compound 3]

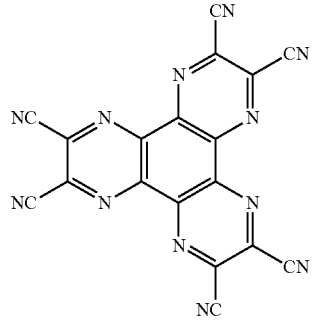

Also, the p-dopant may be one of quinone derivatives, metal oxides, or cyano group-containing compounds, but is not limited thereto. For example, non-limiting examples of the p-dopant may include quinone derivatives such as tetracyanoquinodimethane (TCNQ) and 2,3,5,6-tetrafluoro-7,7,8,8-tetracyanoquinodimethane (F4-TCNQ), metal oxides such as tungsten oxide and molybdenum oxide, etc., but are not limited thereto.

As described above, the hole transport region HTR may further include at least one of a hole buffer layer (not shown) or an electron blocking layer EBL in addition to the hole injection layer HIL and the hole transport layer HTL. The hole buffer layer (not shown), may compensate a resonance distance according to the wavelength of light emitted from an emission layer EML and may increase light emission efficiency. The materials which may be included in the hole transport region HTR may be used as materials which may be included in the hole buffer layer (not shown). The electron blocking layer (not shown) is a layer that serves to prevent or reduce electrons from being injected from the electron transport region ETR to the hole transport region HTR.

The emission layer EML is provided on the hole transport region HTR. The thickness of the emission layer EML may be, for example, from about 100 Å to about 1000 Å or from about 100 Å to about 300 Å. The emission layer EML may have a single layer formed of a single material, a single layer formed of a plurality of different materials, or a multilayer structure having a plurality of layers formed of a plurality of different materials.

In the organic light emitting diode 10, 10a of an embodiment, the emission layer EML may include anthracene derivatives, pyrene derivatives, perylene derivatives, fluoranthene derivatives, chrysene derivatives, dehydrobenzanthracene derivatives, or triphenylene derivatives. Specifically, the emission layer EML may include anthracene derivatives or pyrene derivatives.

In the organic light emitting diode 10, 10a of an embodiment illustrated in FIGS. 1 to 3, the emission layer EML may include a host and a dopant, and the emission layer EML may include a known host material and a known dopant material.

The emission layer EML may further include a general material known in the art as a host material. For example, the emission layer EML may include, as a host material, at least one of bis[2-(diphenylphosphino)phenyl] ether oxide (DPEPO), 4,4'-bis(carbazol-9-yl)biphenyl (CBP), 1,3-bis (carbazol-9-yl)benzene (mCP), 2,8-Bis(diphenylphosphoryl)dibenzo[b,d]furan (PPF), 4,4',4''-tris(carbazol-9-yl)-triphenylamine (TCTA), or 1,3,5-tris(1-phenyl-1H-benzo[d]imidazole-2-yl)benzene (TPBi). However, embodiments are not limited thereto, for example, tris(8-hydroxyquinolino) aluminum (Alq3), poly(N-vinylcarbazole) (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO3), octaphenylcyclotetra siloxane (DPSiO4), etc. may be used as a host material.

The emission layer EML may include anthracene derivatives represented by Formula A below:

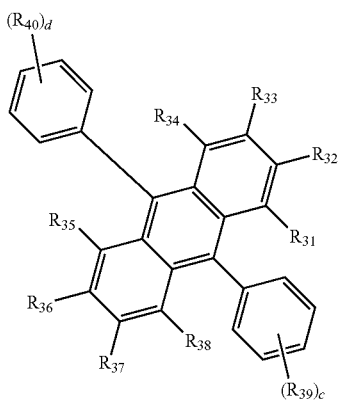

[Formula A]

In Formula A, $R_{31}$ to $R_{40}$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or bonded to an adjacent group to form a ring. Meanwhile, $R_{31}$ to $R_{40}$ may be bonded to an adjacent group to form a saturated hydrocarbon ring or an unsaturated hydrocarbon ring.

In Formula A, c and d may be each independently an integer of 0 to 5.

Formula A may be represented by any one among Compound 3-1 to Compound 3-16 below.

3-1

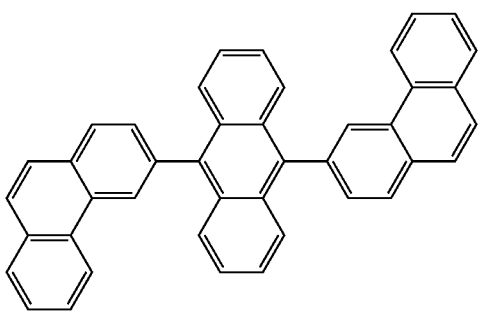

3-2

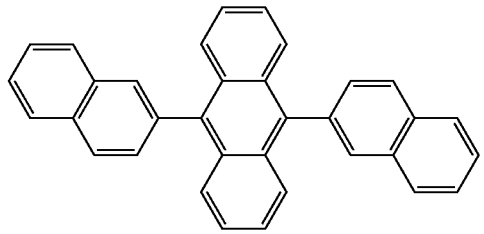

3-3

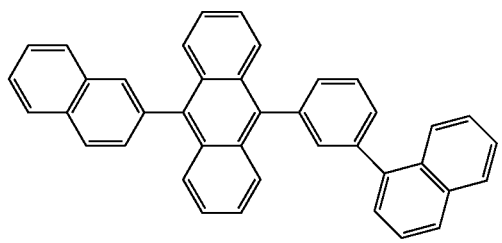

3-4

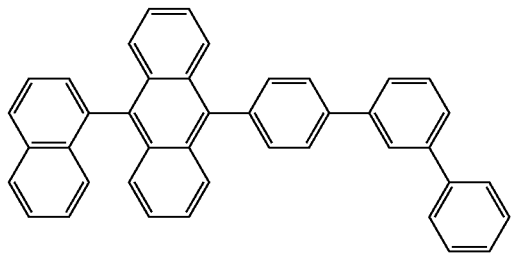

3-5

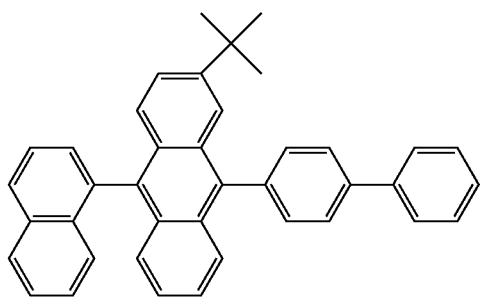

3-6

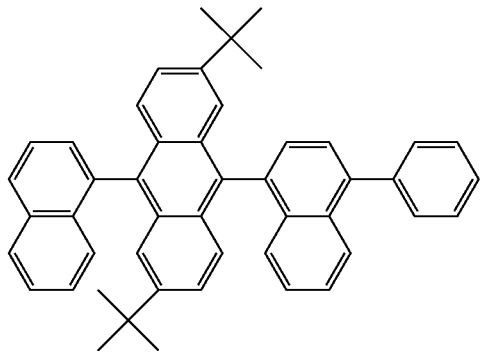

-continued
3-7
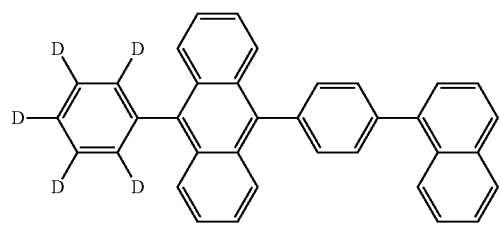
3-8
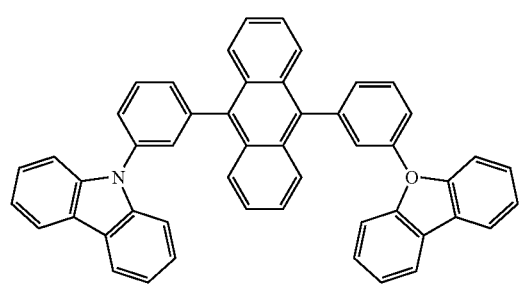
3-9
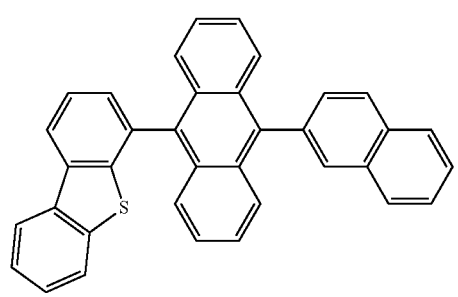
3-10
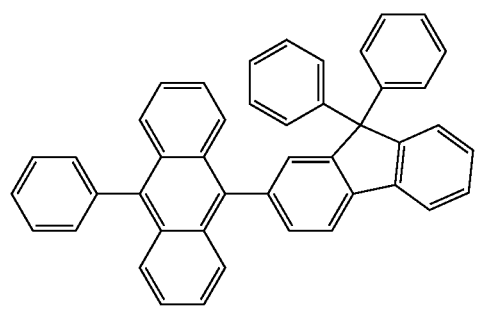
3-11
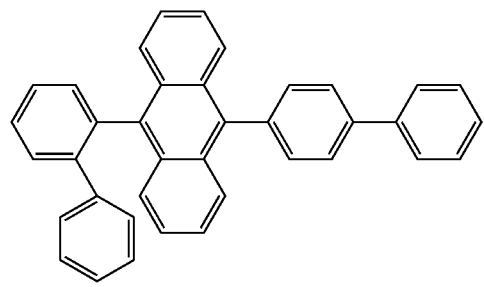
-continued
3-12
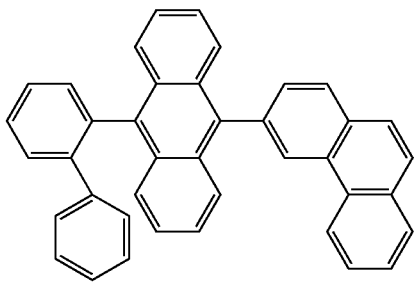
3-13
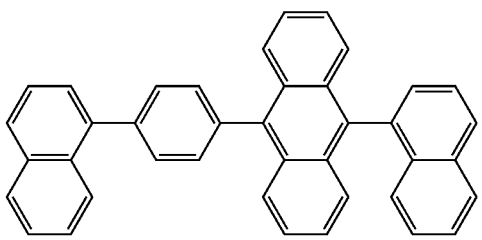
3-14
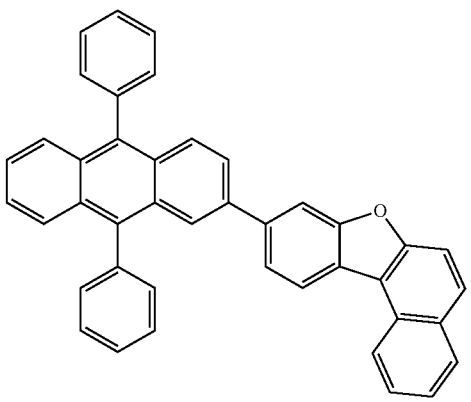
3-15
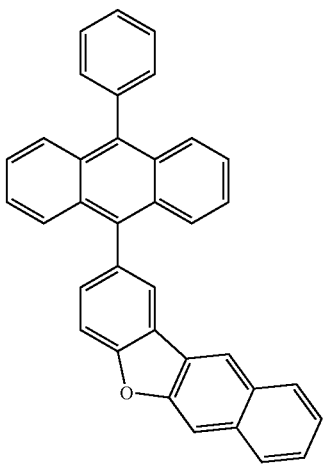

3-16

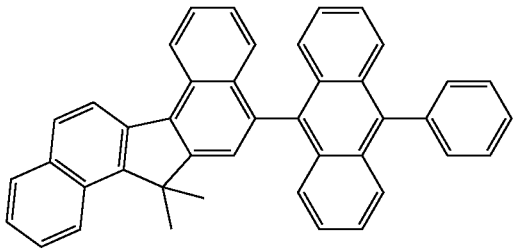

In an embodiment, the emission layer EML may include, as a known dopant material, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and derivatives thereof (e.g., 2,5,8,11-tetra-t-butylperylene (TBP)), pyrene and derivatives thereof (e.g., 1,1-dipyrene, 1,4-dipyrenylbenzene, 1,4-bis(N,N-diphenylamino)pyrene), chrysene and derivatives thereof (e.g., N6,N6,N12,N12-tetrakis(3,4-dimethylphenyl)-3-isopropylchrysene-6,12-diamine), etc.

In the organic light emitting diode 10 of an embodiment illustrated in FIGS. 1 to 3, the electron transport region ETR is provided on the emission layer EML. The electron transport region ETR may include at least one of a hole blocking layer (not shown), an electron transport layer ETL, or an electron injection layer EIL, but an embodiment is not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, and may have a single layer structure formed of an electron injection material and an electron transport material. In addition, the electron transport region ETR may have a single layer structure formed of a plurality of different materials, or may have a structure in which an electron transport layer ETL/electron injection layer EIL and a hole blocking layer (not shown)/electron transport layer ETL/electron injection layer EIL are stacked in order from the emission layer EML, but is not limited thereto. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, a laser induced thermal imaging (LITI) method, etc.

When the electron transport region ETR includes the electron transport layer ETL, the electron transport region ETR may include an anthracene-based compound. However, embodiments are not limited thereto, and the electron transport region may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-yl)phen yl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate) (Bebq2), 9,10-di(naphthalene-2-yl)anthracene (ADN), 1,3-bis[3,5-di(pyridin-3-yl)phenyl]benzene (BmPyPhB), or a mixture thereof. The thickness of the electron transport layers ETL may be from about 100 Å to about 1,000 Å, for example, from about 150 Å to about 500 Å. If the thickness of the electron transport layers ETL satisfies the above-described range, satisfactory electron transport characteristics may be obtained without a substantial increase in driving voltage.

When the electron transport region ETR includes the electron injection layer EIL, the electron transport region ETR may be formed using metal halides such as LiF, NaCl, CsF, RbCl, and RbI, a lanthanide metal such as Yb, metal oxides such as Li$_2$O and BaO, lithium quinolate (LiQ), etc., but an embodiment is not limited thereto. The electron injection layer EIL may also be formed of a mixture material of an electron transport material and an insulating organo-metal salt. The organo-metal salt may be a material having an energy band gap of about 4 eV or more. Specifically, the organo-metal salt may include, for example, metal acetates, metal benzoates, metal acetoacetates, metal acetylacetonates or metal stearates. The thickness of the electron injection layers EIL may be from about 1 Å to about 100 Å, and from about 3 Å to about 90 Å. If the thickness of the electron injection layers EIL satisfies the above-described range, satisfactory electron injection properties may be obtained without a substantial increase in driving voltage.

The electron transport region ETR may include a hole blocking layer (not shown) as described above. The hole blocking layer (not shown) may include, for example, at least one of 2,9-dimethyl-4,7-diphenyl-1,10-phenanthroline (BCP) or 4,7-diphenyl-1,10-phenanthroline (Bphen), but is not limited thereto.

The second electrode EL2 is provided on the electron transport region ETR. The second electrode EL2 may be a common electrode or a cathode. The second electrode EL2 may be a transflective electrode. When the second electrode EL2 is the transflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound thereof or a mixture thereof (e.g., a mixture of Ag and Mg). Alternatively, the first electrode EL1 may have a multilayer structure including a reflective layer or a transflective layer formed of the above-described materials, and a transparent conductive layer formed of ITO, IZO, ZnO, ITZO, etc.

Although not shown, the second electrode EL2 may be connected to an auxiliary electrode. When the second electrode EL2 is connected to the auxiliary electrode, the resistance of the second electrode EL2 may decrease.

Meanwhile, a capping layer CPL may be further disposed on the second electrode EL2 of the organic light emitting diode 10a of an embodiment. The capping layer CPL may include, for example, α-NPD, NPB, TPD, m-MTDATA, Alq3, CuPc, N4,N4,N4',N4'-tetra(biphenyl-4-yl) biphenyl-4,4'-diamine (TPD15), 4,4',4"-tris(carbazol-9-yl)triphenylamine (TCTA), N, N'-bis(naphthalen-1-yl), etc.

Figure 5:
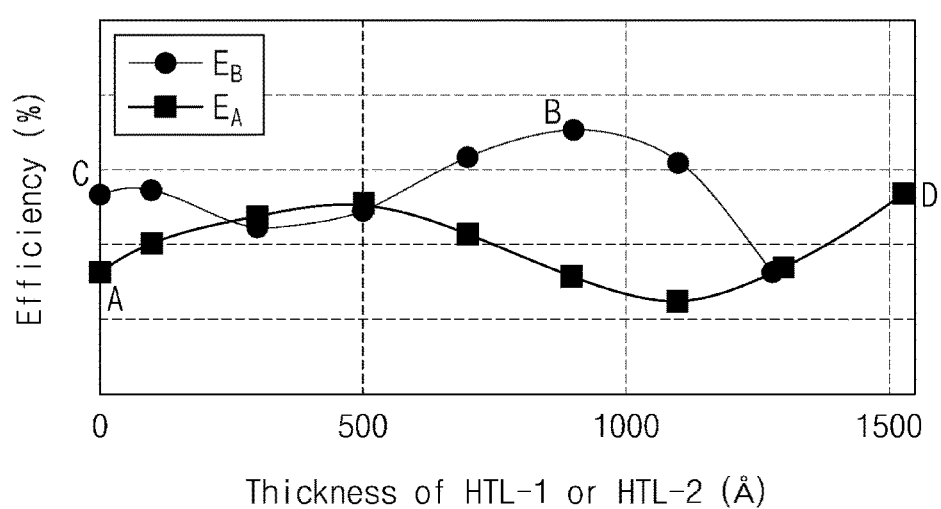
FIG. 5 is a graph illustrating luminous efficiency according to a thickness change and a stacking order of hole transport layers.

FIG. 5 is a graph illustrating each luminous efficiency when the first hole transport layer HTL-1 having a first refractive index of 1.6 and the second hole transport layer HTL-2 having a second refractive index of 1.9 are applied to the organic light emitting diode 10a according to an embodiment.

$E_A$ is a case in which the second hole transport layer HTL-2 is disposed adjacent to the emission layer EML, and $E_B$ is a case in which the first hole transport layer HTL-1 is disposed adjacent to the emission layer EML.

$E_A$ is an organic light emitting diode in which the second hole transport layer HTL-2 is disposed on the first hole transport layer HTL-1, and the emission layer EML is disposed on the second hole transport layer HTL-2. On the contrary, $E_B$ is an organic light emitting diode in which the first hole transport layer HTL-1 is disposed on the second hole transport layer HTL-2, and the emission layer EML is disposed on the first hole transport layer HTL-1.

Point A of $E_A$ has only the second hole transport layer HTL-2 without the first hole transport layer HTL-1, and point C of $E_B$ has the first hole transport layer HTL-1 without the second hole transport layer HTL-2. Point C to which only the first hole transport layer HTL-1 is applied shows improved luminous efficiency compared to point A to which only the second hole transport layer HTL-2 is applied. In addition, point B in which the second hole transport layer HTL-2 is directly disposed on the lower portion of the first hole transport layer HTL-1 shows higher luminous efficiency than point C.

Table 1 shows relative values of luminous efficiency in points A, B, and C illustrated in FIG. 5.

TABLE 1

| Division | Point A | Point B | Point C |
|---|---|---|---|
| Efficiency | 100% | 116% | 109% |

Assuming luminous efficiency at point A to be 100%, relative luminous efficiencies at points B and C are shown in Table 1. As described above, it is confirmed that points B and C including the first hole transport layer HTL-1 have improved luminous efficiency. In addition, it is confirmed that point B in which the second hole transport layer HTL-2 is directly disposed on the lower portion of the first hole transport layer HLT-1 has more improved luminous efficiency than point C.

Figure 4:
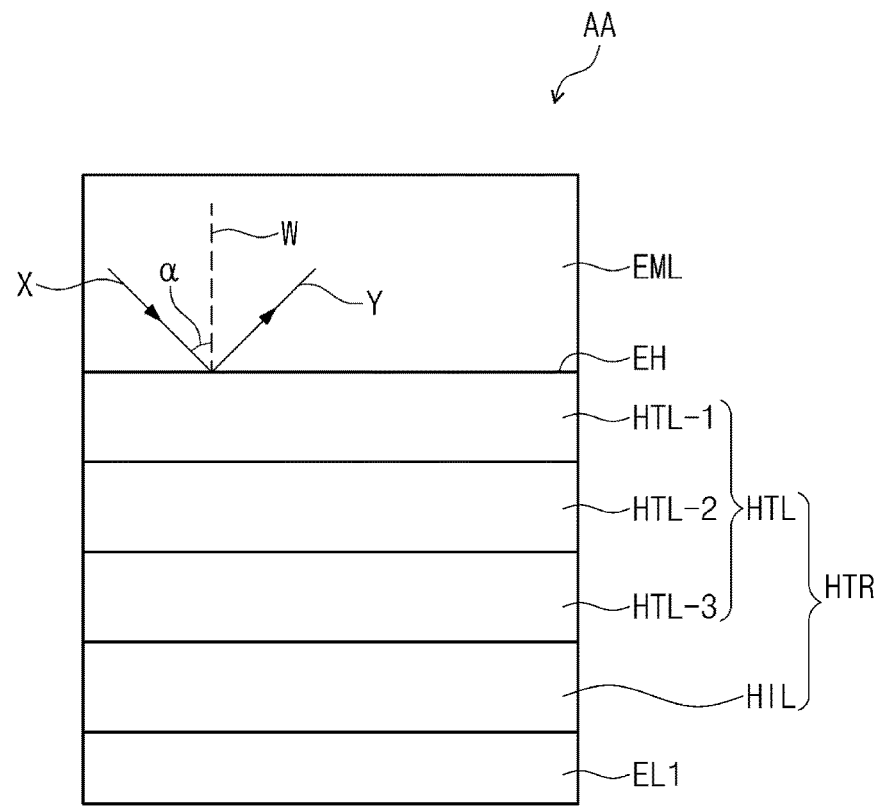
FIG. 4 is a cross-sectional view illustrating a part of an organic light emitting diode according to an embodiment of the inventive concepts.

FIG. 4 is an enlarged cross sectional view illustrating area AA of FIG. 3. FIG. 4 illustrates a scene in which total reflection occurs on the interface EH between the emission layer EML and the first hole transport layer HTL-1 according to an embodiment. It is shown that light X which is generated in the emission layer EML and enters the hole transport region HTR is totally reflected on the interface EH between the emission layer EML and the first hole transport layer HTL-1. As the first refractive index of the first hole transport layer HTL-1 decreases, an angle α between a line W that is perpendicular to the interface EH and an incident light X increases, and as the angle α increases, the incident light X is totally reflected, and thus the amount of light Y which goes upwards may increase.

The first hole transport layer HTL-1 having the relatively low first refractive index is directly disposed on the lower portion of the emission layer EML, and thus the probability in which total reflection of light occurs between the emission layer EML and the first hole transport layer HTL-1 due to a difference in refractive index may increase. When total reflection of light between the emission layer EML and the first hole transport layer HTL-1 increases, the ratio of light moving toward the first electrode EL1 may decrease and the amount of light loss in the inside may be reduced. If the amount of light loss is reduced and the amount of light which is emitted to the outside is increased, an effect of improving luminous efficiency of the organic light emitting diode 10, 10a may be obtained. In addition, the second hole transport layer HTL-2 is disposed to compensate electrical characteristics of the first hole transport layer HTL-1, and light coming towards the first electrode EL1 may be emitted.

The organic light emitting diode of an embodiment may include the fluorene compound of an embodiment described above in the first hole transport layer directly disposed on the lower portion of the emission layer, and the first hole transport layer may have the first refractive index from 1.2 to 1.7. Also, the organic light emitting diode of an embodiment may further include the second hole transport layer HTL-2 which has the second refractive index greater than the first refractive index on the lower portion of the first hole transport layer to exhibit improved luminous efficiency of the organic light emitting diode.

The organic light emitting diode of an embodiment may include a plurality of hole transport layers having different refractive indexes, thereby exhibiting device characteristics having improved luminous efficiency.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An organic light emitting diode comprising:
a first electrode;
a hole transport region disposed on the first electrode;
an emission layer disposed on the hole transport region;
an electron transport region disposed on the emission layer; and
a second electrode disposed on the electron transport region,
wherein the hole transport region comprises:
a first hole transport layer having a first refractive index; and
a second hole transport layer having a second refractive index greater than the first refractive index and being disposed under the first hole transport layer,
wherein the first hole transport layer comprises a fluorene compound represented by Formula 1 below:

[Formula 1]

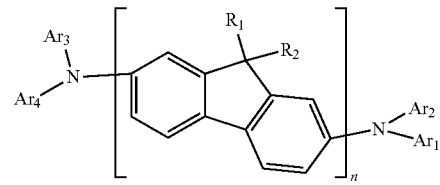

wherein, in Formula 1 above,
$R_1$ and $R_2$ are each independently a substituted or unsubstituted alkyl group having 1 to 30 carbon atoms,
n is an integer of 1 to 3, and
$Ar_1$ to $Ar_4$ are each independently a hydrogen atom, a deuterium atom, a halogen atom, a cyano group, a substituted or unsubstituted amino group, a substituted or unsubstituted aryl group having 6 to 60 carbon atoms, a substituted or unsubstituted heterocyclic group having 2 to 60 carbon atoms, or are bonded to an adjacent group to form a ring, and wherein $R_1$ and $R_2$ are each independently an unsubstituted n-butyl group or a n-pentyl group substituted with $CF_3$, when n is 1.

2. The organic light emitting diode of claim 1, wherein the first hole transport layer is directly disposed under the emission layer.

3. The organic light emitting diode of claim 1, wherein a ratio of a thickness $T_1$ of the first hole transport layer and a thickness $T_2$ of the second hole transport layer satisfies a relationship of Expression 1 below:

$$1 \leq T_2/T_1 \leq 3. \qquad [\text{Expression 1}]$$

4. The organic light emitting diode of claim 1, wherein a difference between the first refractive index and the second refractive index is at least 0.2.

5. The organic light emitting diode of claim 4, wherein the first refractive index is from 1.2 to 1.7, and the second refractive index is from 1.7 to 1.9.

6. The organic light emitting diode of claim 1, wherein the fluorene compound is any one among the compounds represented by Compound Group 1 below:

[Compound Group 1]

3

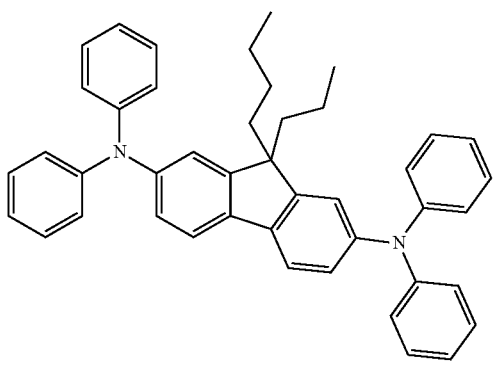

4

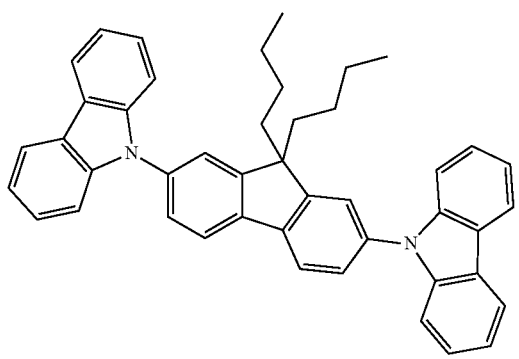

6

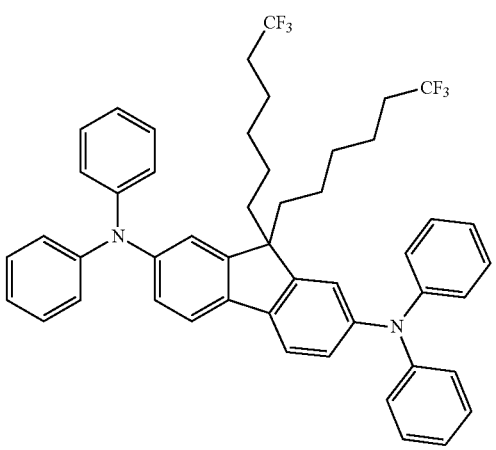

7

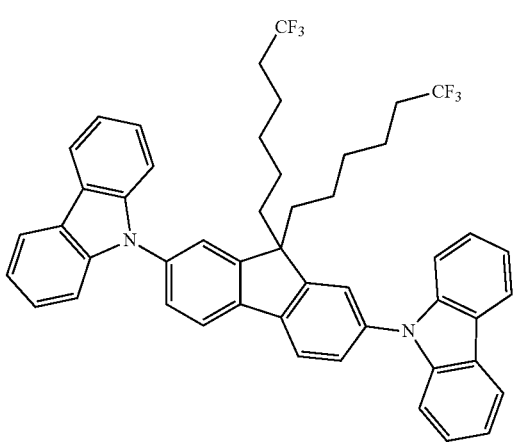

8

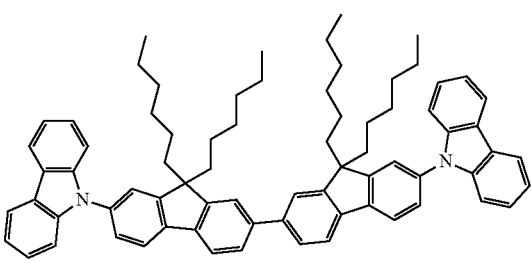

7. The organic light emitting diode of claim 1, wherein the second hole transport layer comprises a compound represented by Formula 2 below:

[Formula 2]

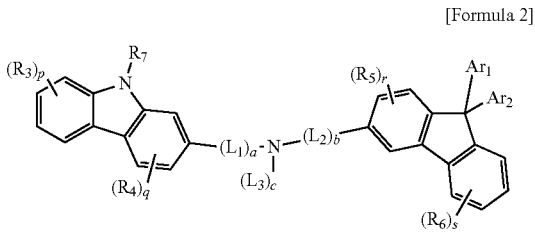

wherein, in Formula 2 above, $Ar_1$ and $Ar_2$ are a hydrogen atom, a deuterium atom, a halogen atom, a substituted or unsubstituted alkyl group having 1 to 30 carbon atoms, a substituted or unsubstituted aryl group having 6 to 30 carbon atoms, or bonded to an adjacent group to form a ring, a to c are each independently an integer of 0 to 5, $L_1$ and $L_2$ are each independently a substituted or unsubstituted cycloalkylene group having 3 to 10 ring-forming carbon atoms, a substituted or unsubstituted heterocycloalkylene group having 2 to 10 ring-forming carbon atoms, a substituted or unsubstituted cycloalkenylene group having 3 to 10 ring-forming carbon atoms, a substituted or unsubstituted arylene group having 6 to 30 ring-forming carbon atoms, or a substituted or unsubstituted heteroarylene group having 2 to 60 ring-forming carbon atoms, $L_3$ is a substituted or unsubstituted cycloalkyl group having 3 to 10 ring-forming carbon atoms, a substituted or unsubstituted heterocycloalkyl group having 2 to 10 ring-forming carbon atoms, a substituted or unsubstituted cycloalkenyl group having 3 to 10 ring-forming carbon atoms, a substituted or unsubstituted aryl group having 6 to 30 ring-forming carbon atoms, or a substituted or unsubstituted heteroaryl group having 2 to 60 ring-forming carbon atoms, p and s are each independently an integer of 0 to 3, q and r are each independently an integer of 0 to 4, and $R_3$ to $R_7$ are each independently a hydrogen atom, a deuterium atom, a halogen atom, a hydroxy group, a cyano group, a nitro group, an amino group, a substituted or unsubstituted silyl group, a substituted or unsubstituted oxy group, a substituted or unsubstituted alkyl group having 1 to 60 carbon atoms, a substituted or unsubstituted heterocycloalkyl group having 3 to 60 ring-forming carbon atoms, a substituted or unsubstituted aryl group having 6 to 60 ring-forming carbon atoms, or a substituted or unsubstituted heteroaryl group having 2 to 60 ring-forming carbon atoms.

8. The organic light emitting diode of claim 7, wherein the compound represented by Formula 2 above is any one among the compounds represented by Compound Group 2 below:

[Compound Group 2]

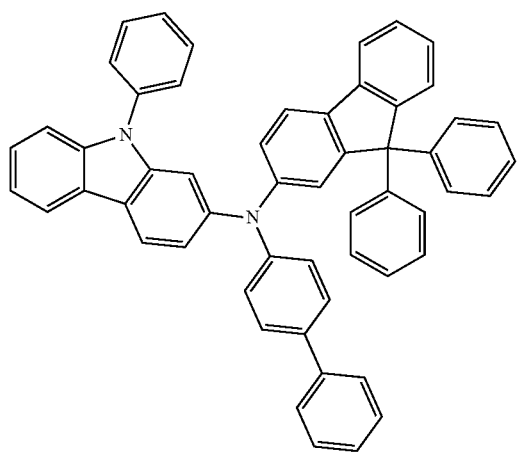

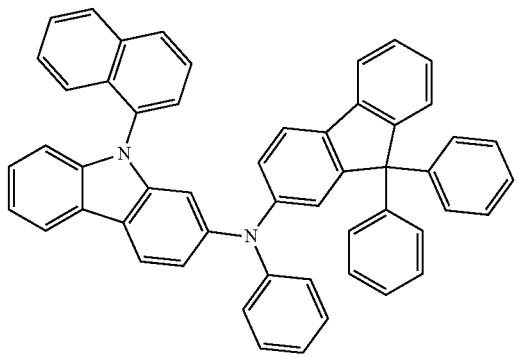

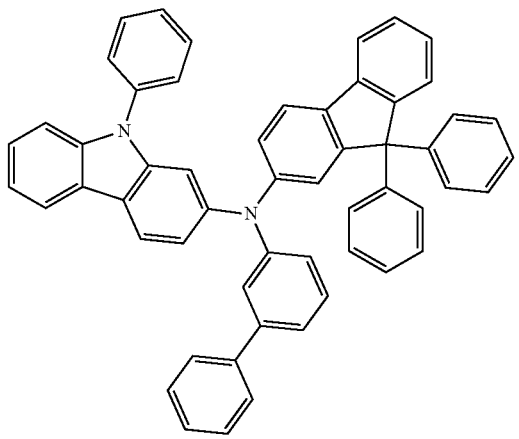

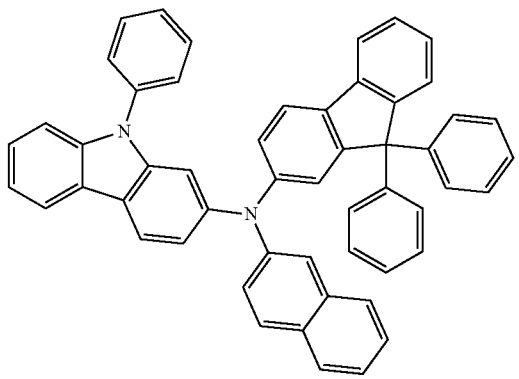

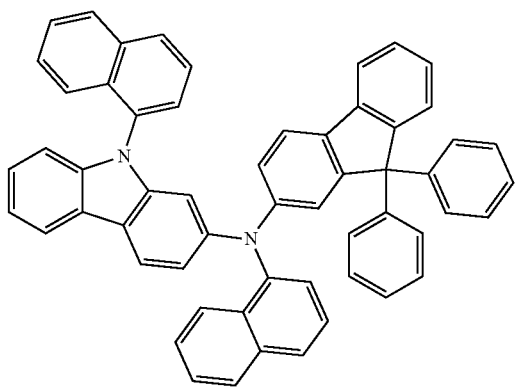

14
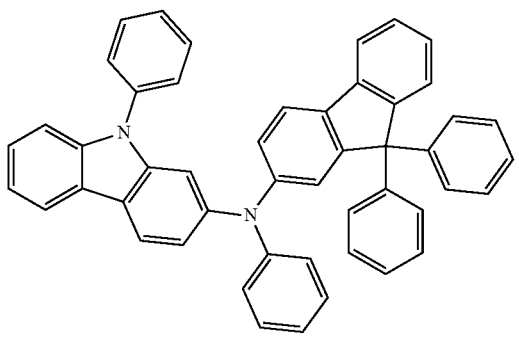
15
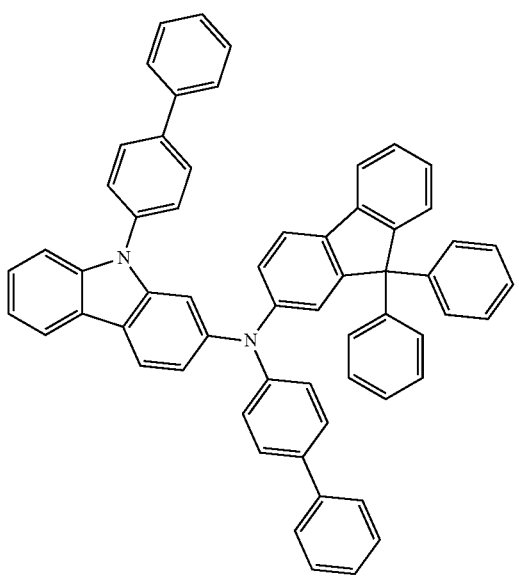
16
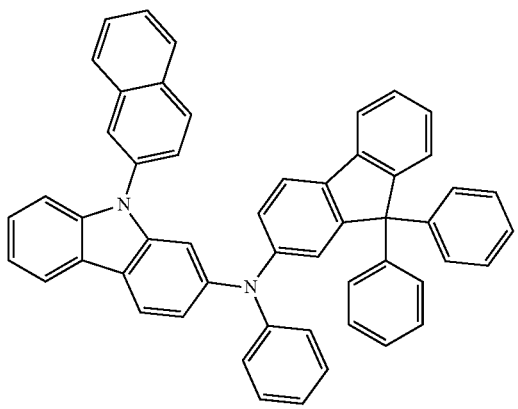
17
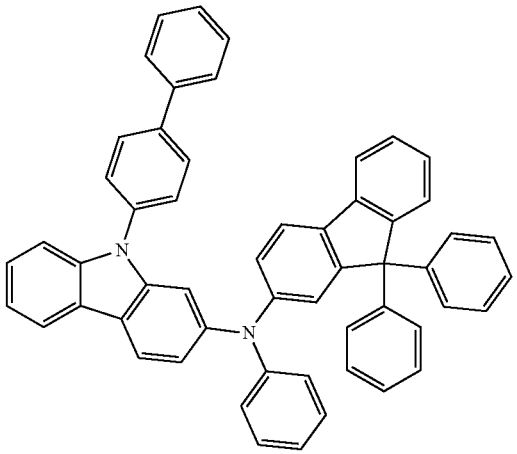
18
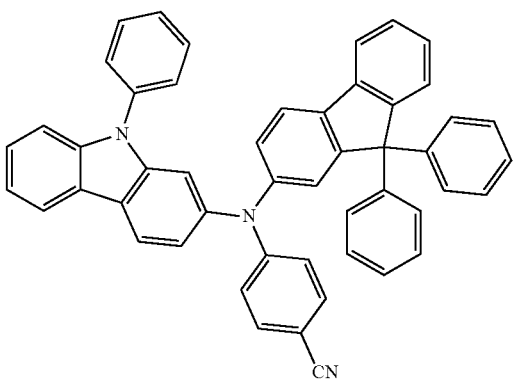
19
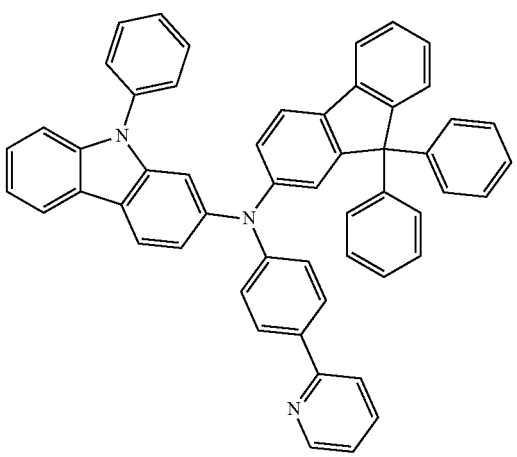

20
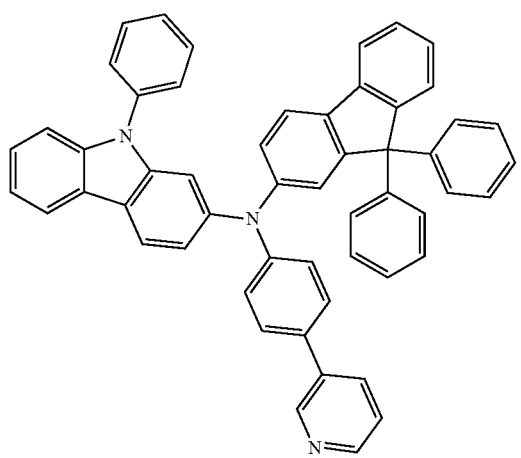
21
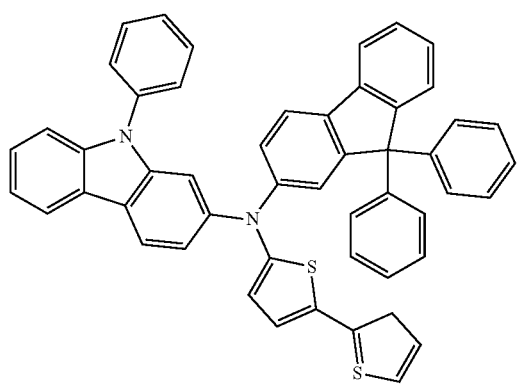
22
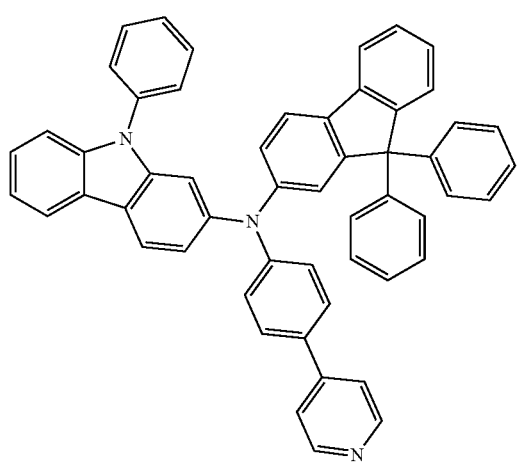
23
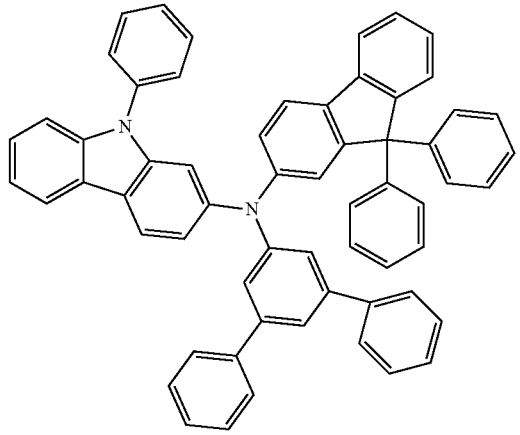
24
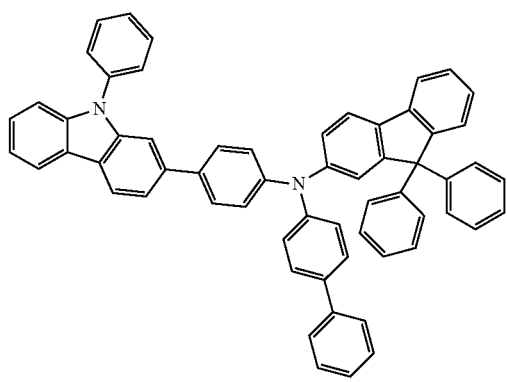
25
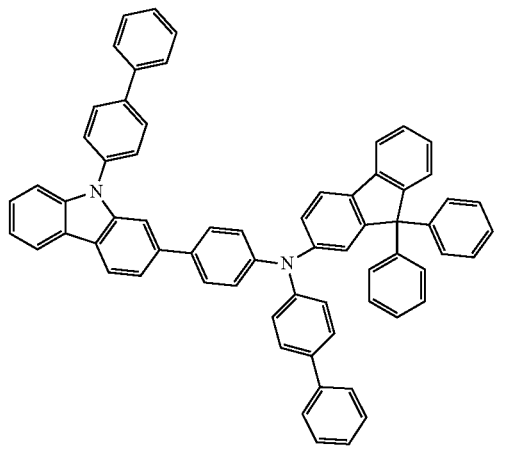
26
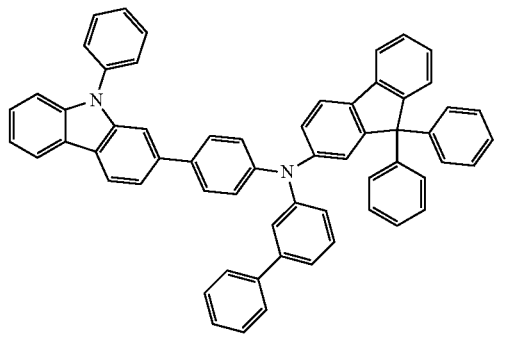

27
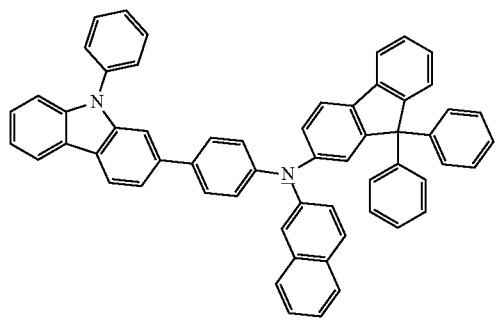
28
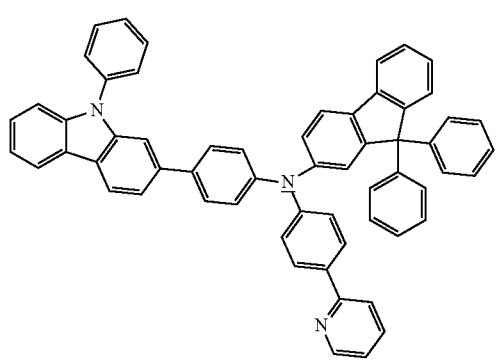
29
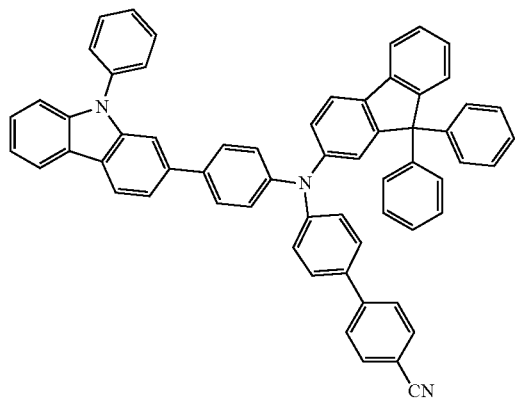
30
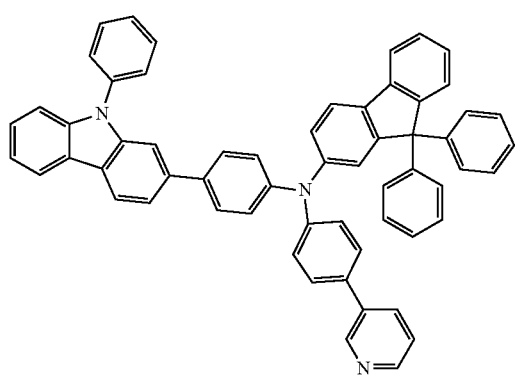
31
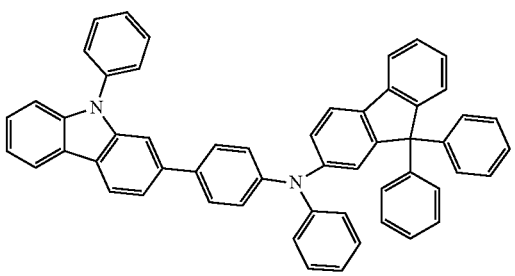
32
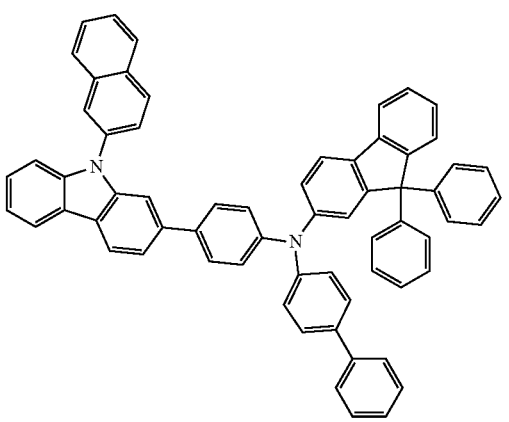
33
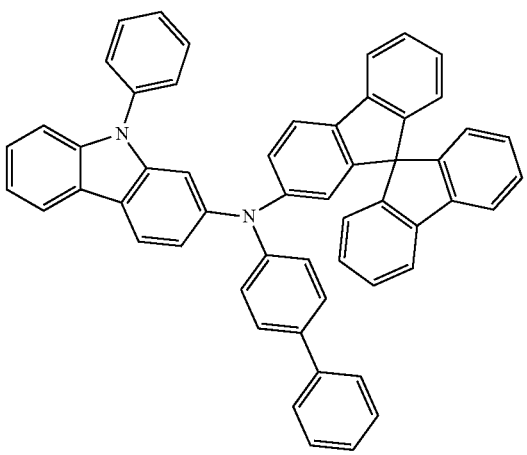
34
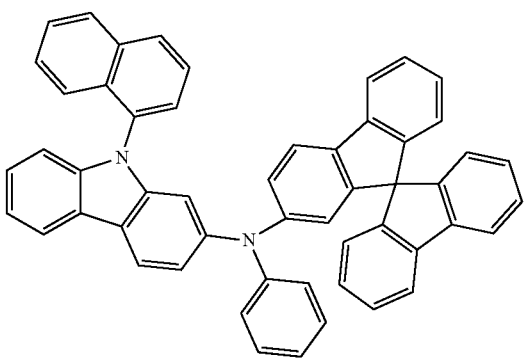

35
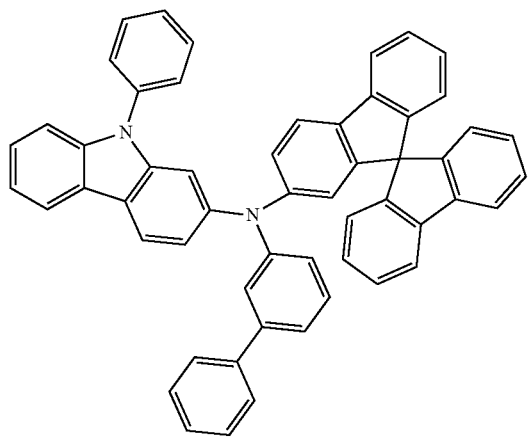
36
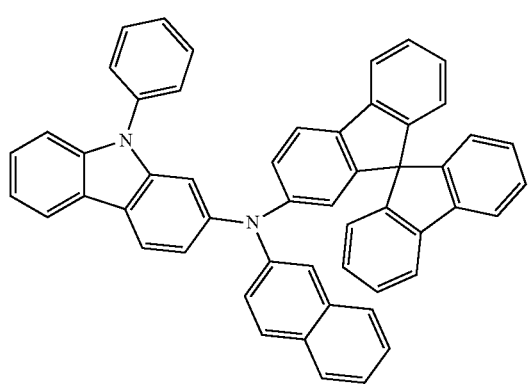
37
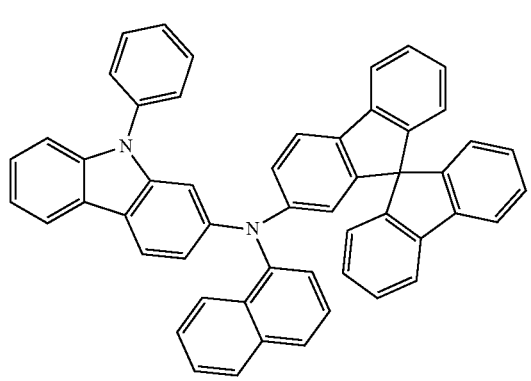
38
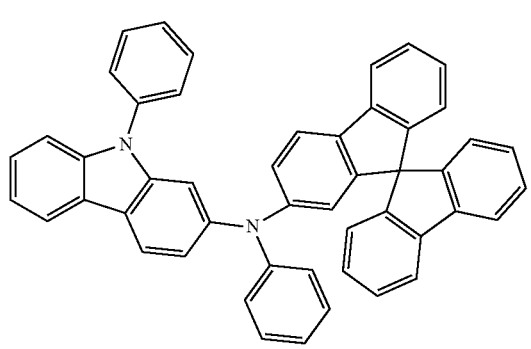
39
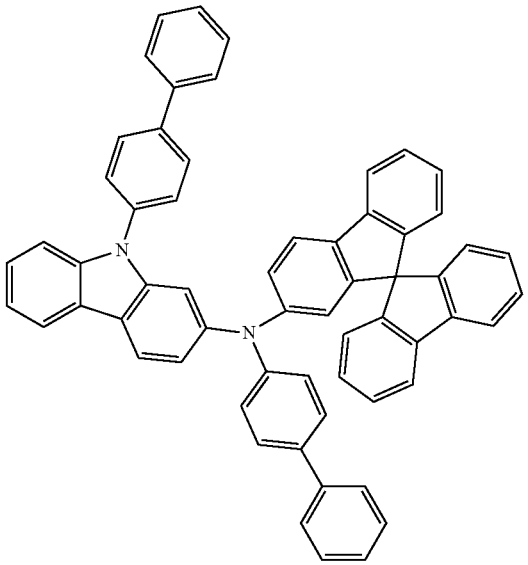
40
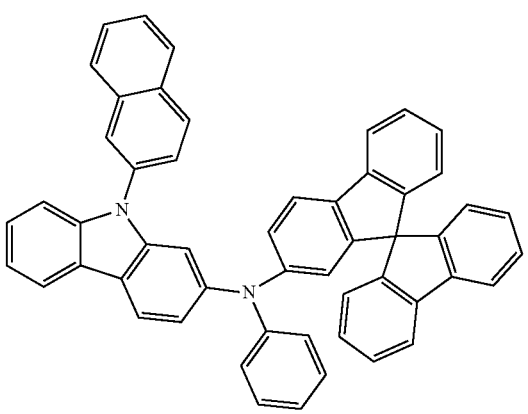
41
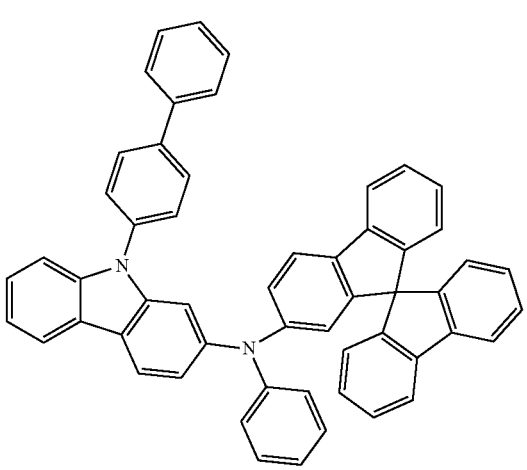

-continued
42
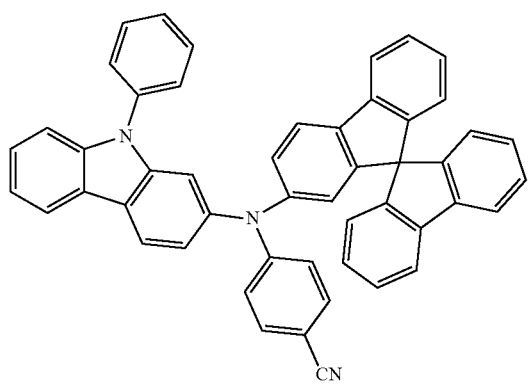
45
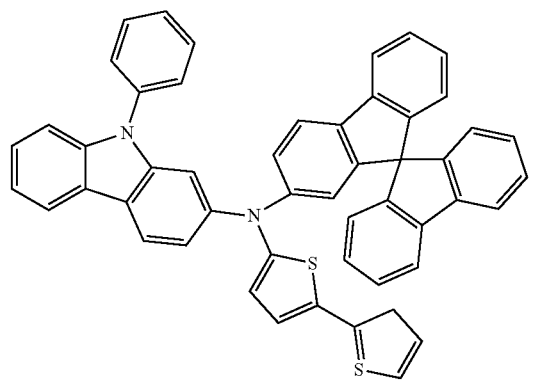
43
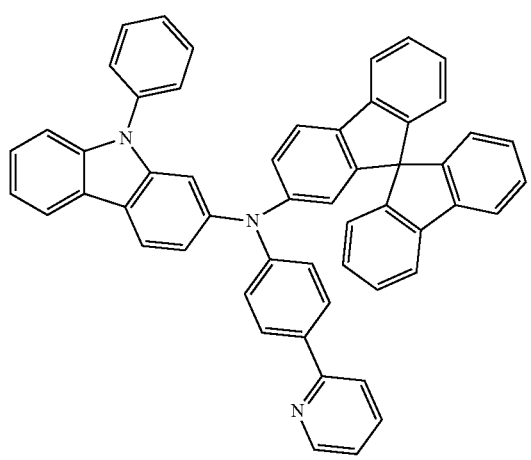
46
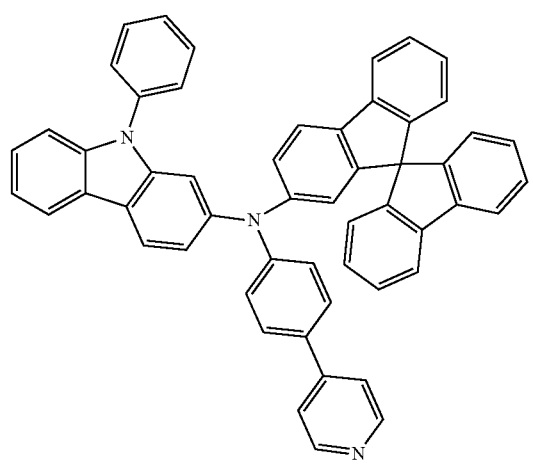
44
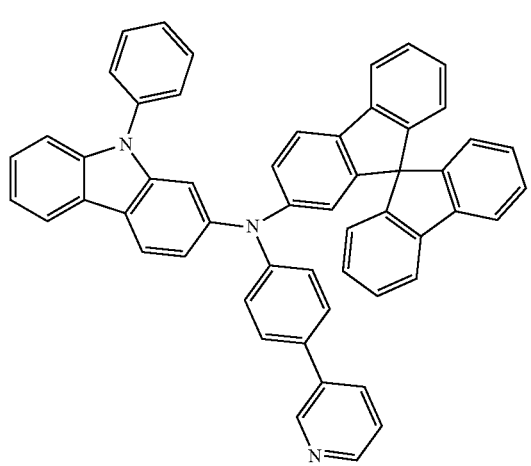
47
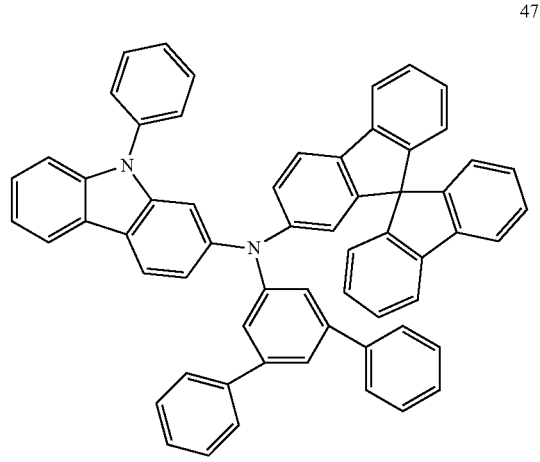

48
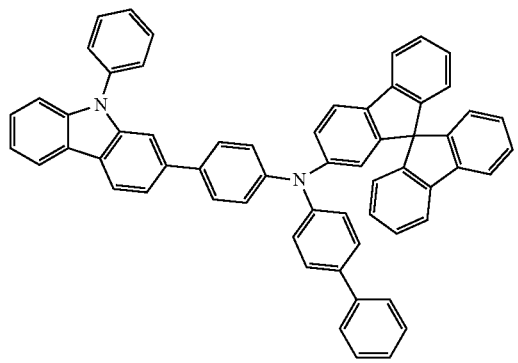
49
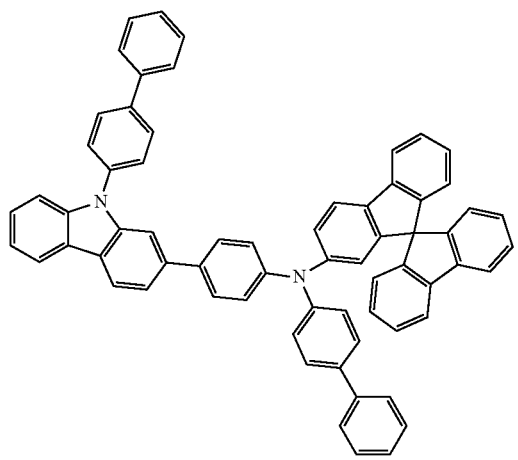
50
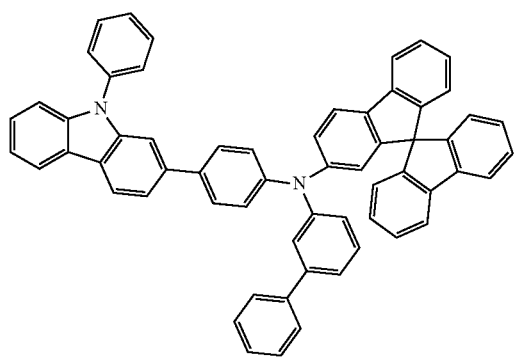
51
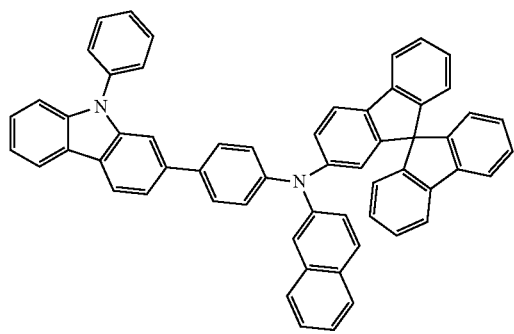
52
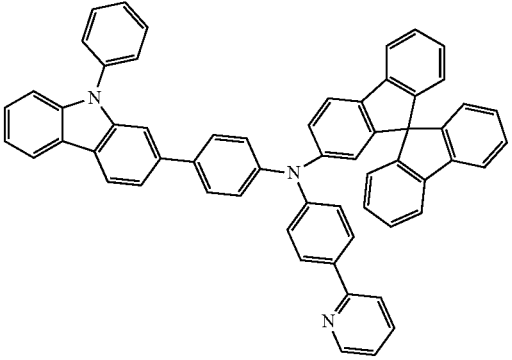
53
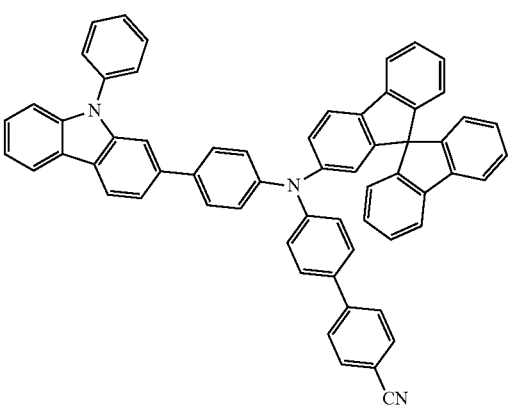
54
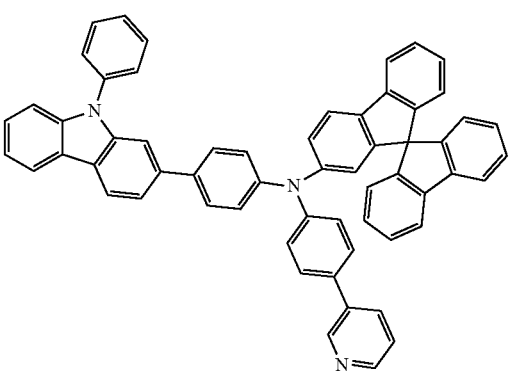
55
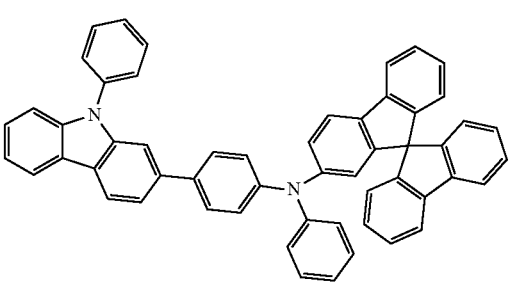

56
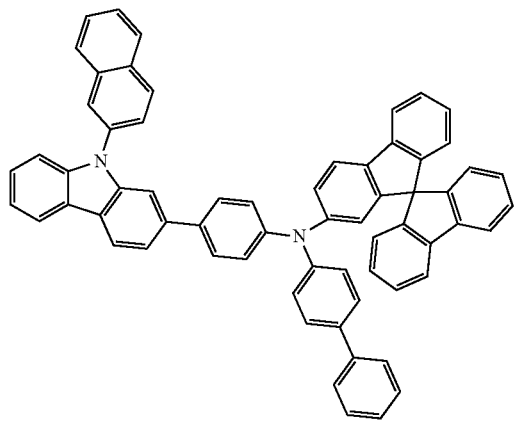
57
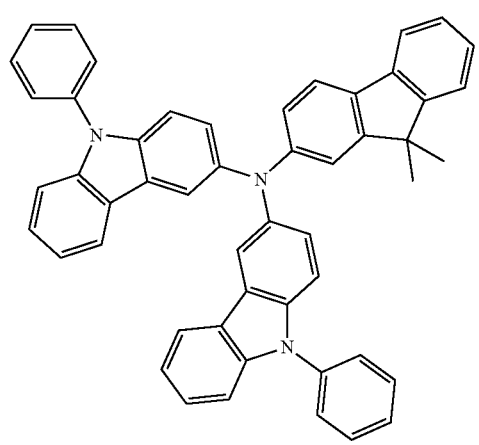
58
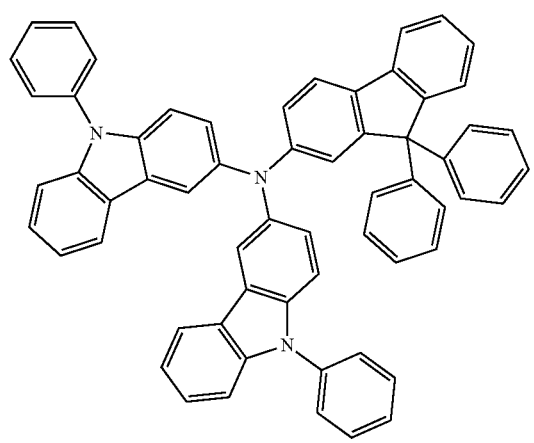
59
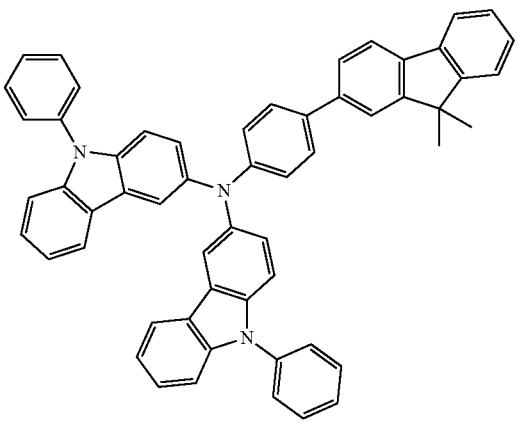
60
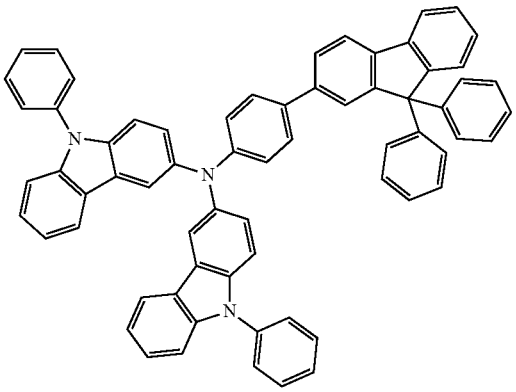
61
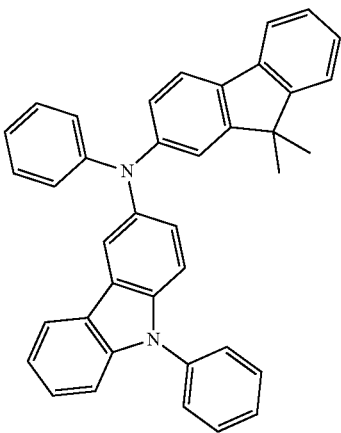

62
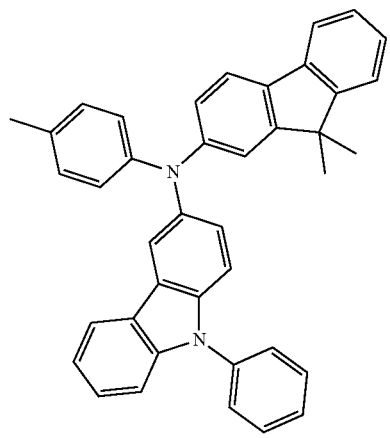
63
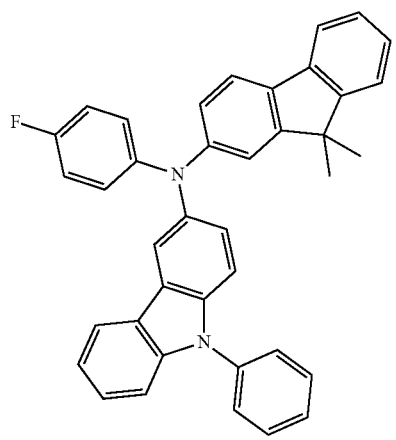
64
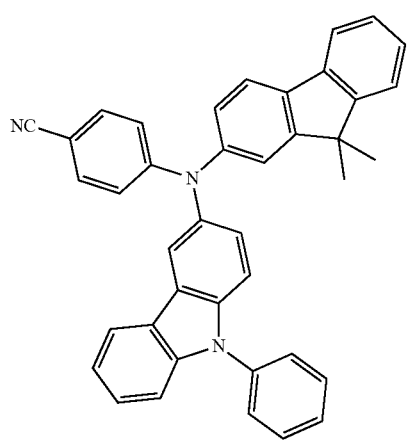
65
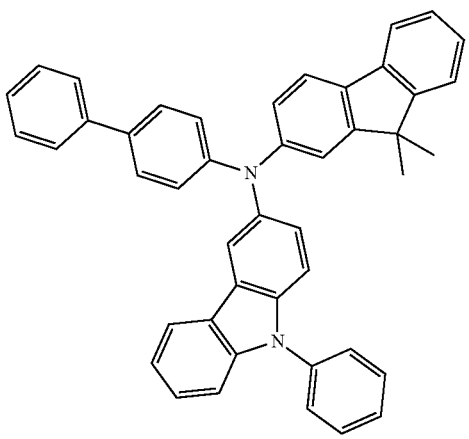
66
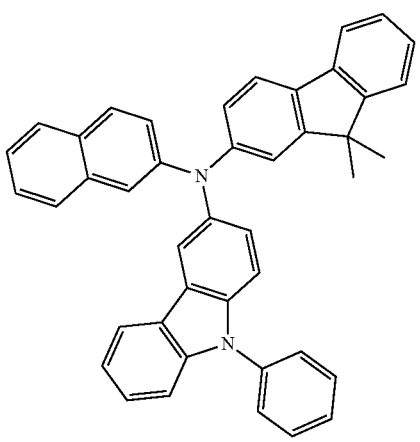
67
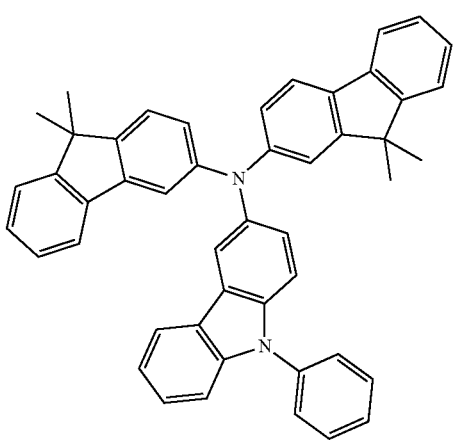

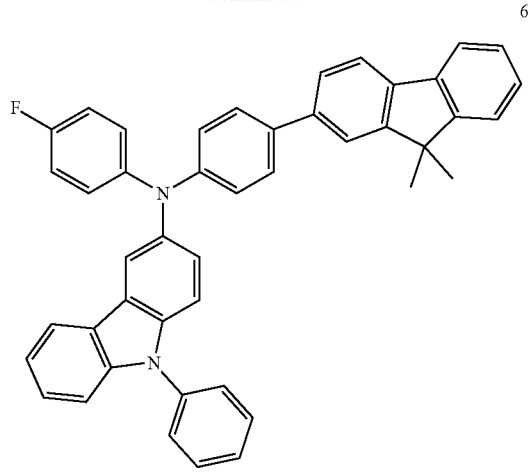
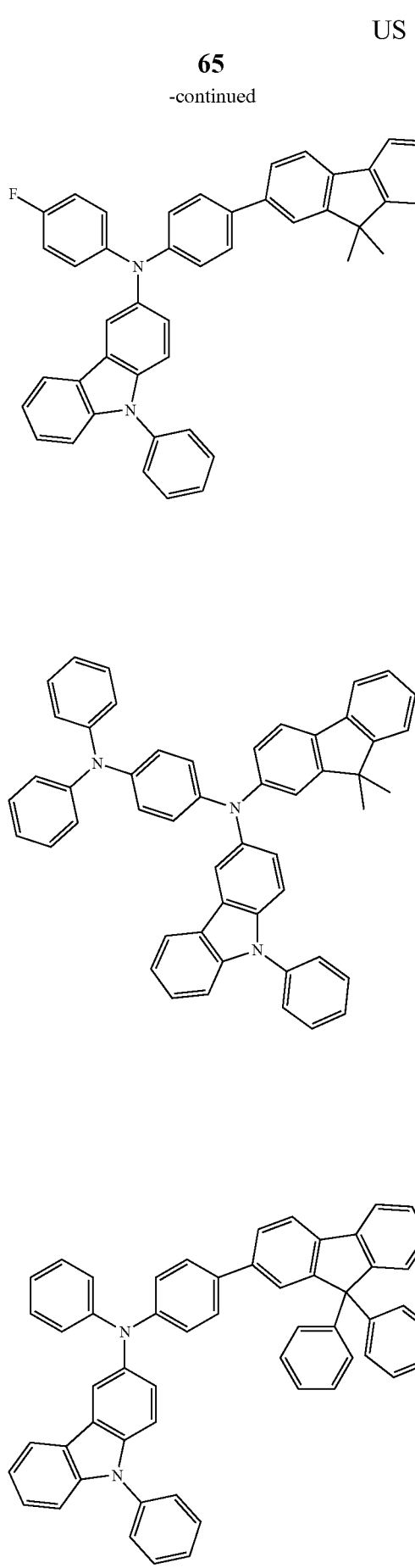
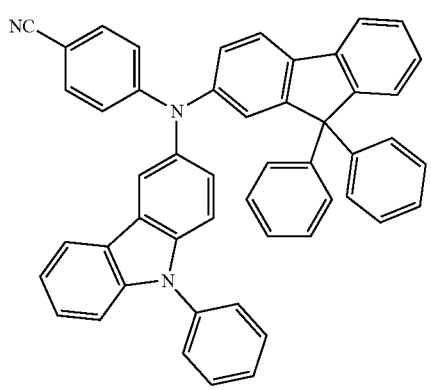
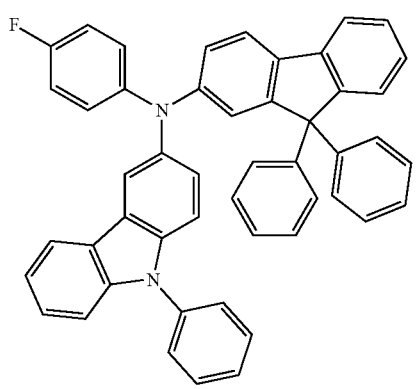
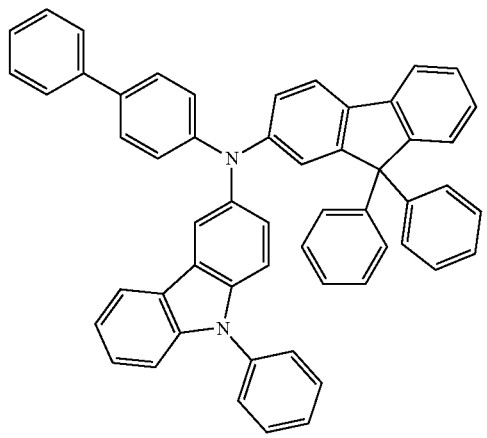
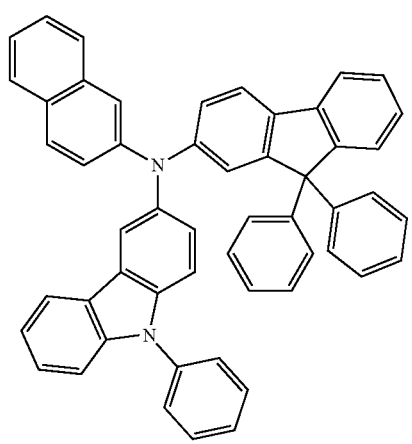

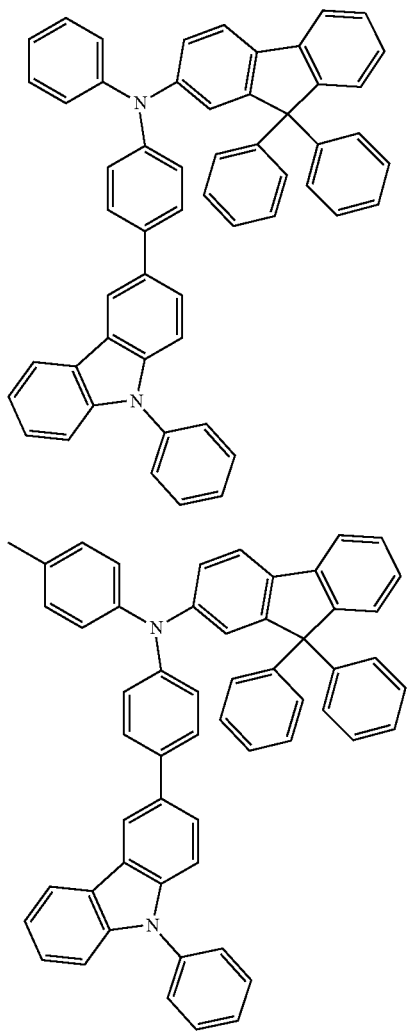

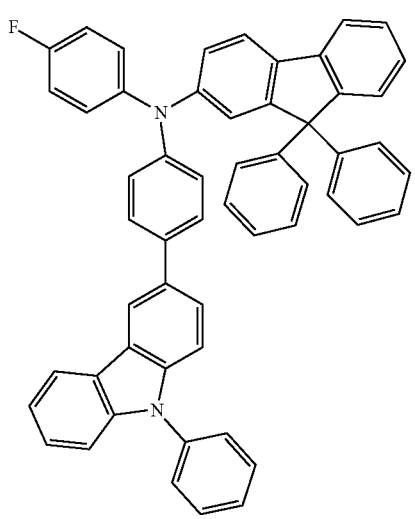

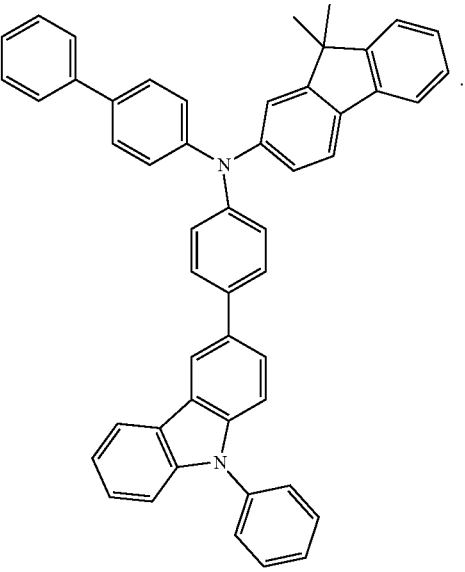

9. The organic light emitting diode of claim 1, wherein the hole transport region further comprises a third hole transport layer disposed under the second hole transport layer, and the third hole transport layer comprises a p-dopant.

10. The organic light emitting diode of claim 1, wherein a difference of a refractive index between the emission layer and the first hole transport layer is at least 0.2.

11. An organic light emitting diode comprising:
a first electrode;
a hole transport region disposed on the first electrode;
an emission layer disposed on the hole transport region;
an electron transport region disposed on the emission layer; and
a second electrode disposed on the electron transport region,
wherein the hole transport region comprises a plurality of hole transport layers having different refractive indexes, and
a layer, among the plurality of the hole transport layers, which is adjacent to the emission layer comprises a fluorene compound represented by Formula 1 below:

[Formula 1]

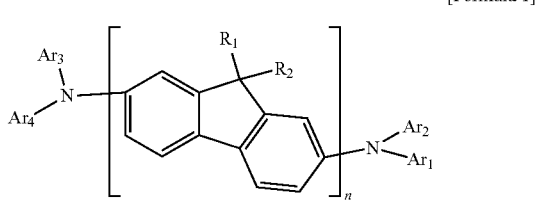

wherein, in Formula 1 above,
$R_1$ and $R_2$ are each independently a substituted or unsubstituted alkyl group having 1 to 30 carbon atoms,
n is an integer of 1 to 3, and
$Ar_1$ to $Ar_4$ are each independently a hydrogen atom, a deuterium atom, a halogen atom, a cyano group, a substituted or unsubstituted amino group, a substituted or unsubstituted aryl group having 6 to 60 carbon atoms, a substituted or unsubstituted heterocyclic group having 2 to 60 carbon atoms, or are bonded to an adjacent group to form a ring, and wherein $R_1$ and $R_2$ are each independently an unsubstituted n-butyl group or a n-pentyl group substituted with $CF_3$, when n is 1.

12. The organic light emitting diode of claim 11, wherein the hole transport region comprises:
   a first hole transport layer having a first refractive index; and
   a second hole transport layer which has a second refractive index greater than the first refractive index and is disposed under the first hole transport layer.

13. The organic light emitting diode of claim 12, wherein a ratio of a thickness $T_1$ of the first hole transport layer and a thickness $T_2$ of the second hole transport layer satisfies a relationship of Expression 1 below:

$$1 \leq T_2/T_1 \leq 3.$$ [Expression 1]

14. The organic light emitting diode of claim 12, wherein a minimum value of a difference between the first refractive index and the second refractive index is 0.2.

15. The organic light emitting diode of claim 14, wherein the first refractive index is from 1.2 to 1.7, and the second refractive index is from 1.7 to 1.9.

16. The organic light emitting diode of claim 12, wherein the second hole transport layer comprises a compound represented by Formula 2 below:

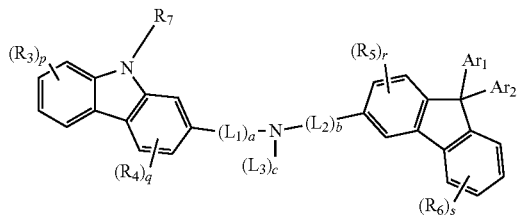

[Formula 2]

wherein, in Formula 2 above, $Ar_1$ and $Ar_2$ are a hydrogen atom, a deuterium atom, a halogen atom, a substituted or unsubstituted alkyl group having 1 to 30 carbon atoms, a substituted or unsubstituted aryl group having 6 to 30 carbon atoms, or bonded to an adjacent group to form a ring, a to c are each independently an integer of 0 to 5, $L_1$ and $L_2$ are each independently a substituted or unsubstituted cycloalkylene group having 3 to 10 ring-forming carbon atoms, a substituted or unsubstituted heterocycloalkylene group having 2 to 10 ring-forming carbon atoms, a substituted or unsubstituted cycloalkenylene group having 3 to 10 ring-forming carbon atoms, a substituted or unsubstituted arylene group having 6 to 30 ring-forming carbon atoms, or a substituted or unsubstituted heteroarylene group having 2 to 60 ring-forming carbon atoms, $L_3$ is a substituted or unsubstituted cycloalkyl group having 3 to 10 ring-forming carbon atoms, a substituted or unsubstituted heterocycloalkyl group having 2 to 10 ring-forming carbon atoms, a substituted or unsubstituted cycloalkenyl group having 3 to 10 ring-forming carbon atoms, a substituted or unsubstituted aryl group having 6 to 30 ring-forming carbon atoms, or a substituted or unsubstituted heteroaryl group having 2 to 60 ring-forming carbon atoms, p and s are each independently an integer of 0 to 3, q and r are each independently an integer of 0 to 4, and $R_3$ to $R_7$ are each independently a hydrogen atom, a deuterium atom, a halogen atom, a hydroxy group, a cyano group, a nitro group, an amino group, a substituted or unsubstituted silyl group, a substituted or unsubstituted oxy group, a substituted or unsubstituted alkyl group having 1 to 60 carbon atoms, a substituted or unsubstituted heterocycloalkyl group having 3 to 60 ring-forming carbon atoms, a substituted or unsubstituted aryl group having 6 to 60 ring-forming carbon atoms, or a substituted or unsubstituted heteroaryl group having 2 to 60 ring-forming carbon atoms.

17. The organic light emitting diode of claim 12, wherein the hole transport region further comprises a third hole transport layer disposed under the second hole transport layer, and the third hole transport layer comprises a p-dopant.

* * * * *